United States Patent
Suzuki et al.

[11] Patent Number: 5,945,434
[45] Date of Patent: Aug. 31, 1999

[54] INDAZOLE DERIVATIVES HAVING MONOCYCLIC AMINE

[75] Inventors: Masashi Suzuki; Masahiro Ueno; Ryuta Fukutomi; Hiroaki Satoh; Haruhiko Kikuchi; Koichiro Hagihara; Takeo Arai; Sugure Taniguchi; Setsuko Mino; Yumiko Noguchi, all of Ohimachi, Japan

[73] Assignee: Nisshin Flour Milling Co., Ltd., Tokyo, Japan

[21] Appl. No.: 08/952,509

[22] PCT Filed: May 31, 1996

[86] PCT No.: PCT/JP96/01475

§ 371 Date: Nov. 28, 1997

§ 102(e) Date: Nov. 28, 1997

[87] PCT Pub. No.: WO96/38420

PCT Pub. Date: Dec. 5, 1996

[30] Foreign Application Priority Data

May 31, 1995 [JP] Japan ................................ 7-155493
Jan. 31, 1996 [JP] Japan ................................ 8-035739

[51] Int. Cl.$^6$ ............... C07D 231/56; C07D 401/12; A61K 31/445
[52] U.S. Cl. ........................ 514/322; 546/199
[58] Field of Search ................. 546/199; 514/322

[56] References Cited

U.S. PATENT DOCUMENTS

| | | | |
|---|---|---|---|
| 3,145,215 | 8/1964 | Kirchner et al. | 260/310 |
| 5,002,948 | 3/1991 | Perregaard et al. | 514/254 |
| 5,017,573 | 5/1991 | Kon et al. | 514/218 |
| 5,166,341 | 11/1992 | Kon et al. | 540/575 |
| 5,654,320 | 8/1997 | Catlow et al. | 514/322 |
| 5,684,003 | 11/1997 | Kikuchi et al. | 514/230.5 |

FOREIGN PATENT DOCUMENTS

| | | |
|---|---|---|
| 2-225460 | 7/1990 | Japan . |
| 2-256670 | 10/1990 | Japan . |
| 6-135960 | 5/1994 | Japan . |
| WO 93/03725 | 3/1993 | WIPO . |
| WO 93/12785 | 7/1993 | WIPO . |

OTHER PUBLICATIONS

Joel Bockaert, John R. Fozard, Aline Dumuis and David E. Clarke, TiPS Reviews, vol. 13 (Apr. 1992). The 5–HT$_4$ receptor: a place in the sun, pp. 141–145.

N.J. Talley. Aliment. Pharmacol. Ther,(Jan. 1992). Review article: 5–hydroxtryptamine agonists and antagonists in the modulation of gastrointestinal motility and sensation: clinical implications, pp. 273–289.

Anthony P.D.W. Ford and David E. Clarke, Medicinal Research Reviews, vol. 13, No. 6 (1993). The 5–HT$_4$ Receptor, pp. 633–662.

*Primary Examiner*—Richard L. Raymond
*Assistant Examiner*—Deepak R. Rao
*Attorney, Agent, or Firm*—Oblon, Spivak, McClelland, Maier & Neustadt, P.

[57] ABSTRACT

An indazole compound having the formula (I):

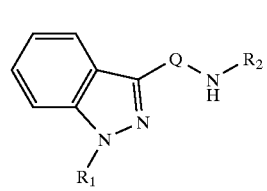

(I)

wherein:

R$_1$ is hydrogen, C$_1$–C$_6$ alkyl, C$_3$–C$_6$ alkenyl or C$_3$–C$_6$ cycloalkyl;

Q is carbonyl, thiocarbonyl or methylene; and

R$_2$ is a group of the formula (II) or (IV);

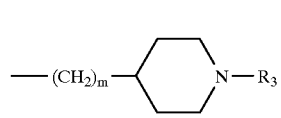

(II)

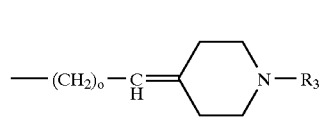

(IV)

wherein R$_1$ is C$_1$–C$_6$ alkyl, C$_3$–C$_6$ alkenyl or benzyl, of which a phenyl group thereof is optionally mono- or di-substituted by the same or different halogen or methoxy; m is 0 to 2; n and o is 1 or 2. The compound exhibits 5-HT$_4$ receptor agonist activity.

11 Claims, No Drawings

INDAZOLE DERIVATIVES HAVING MONOCYCLIC AMINE

TECHNICAL FIELD

This invention relates to a new indazole derivative having a monocyclic amine, a pharmaceutically acceptable salt thereof and a process for the preparation thereof.

The invention further relates to a 5-$HT_4$ receptor agonist, in particular, an agent for the treatment of digestive tract diseases which comprise as an active ingredient the indazole derivative or the salt thereof.

The invention furthermore relates to a method for the treatment of gastrointestinal disorders which comprises administering the indazole derivative or the salt thereof to the patients suffering from gastrointestinal disorders.

BACKGROUND ART

The abnormality in a gastrointestinal motor function by various causes such as chronic gastritis, gastrectomy, peptic ulcer, diabetes mellitus or scleroderma results in the reflux of gastric contents into the esophagus, delayed emptying of the contents and the depression of small and large intestinal functions.

This can lead to several gastrointestinal disorders including nausea, vomiting, heartburn, anorexia, abdominal distension, epigastric dysphoria, abdominaglia, constipation and further reflux esophagitis. One cause of the diseases such as irritable bowel syndrome and spurious ileus is considered to be the depression in gastrointestinal motility.

The agents for the treatment of these conditions and diseases include direct cholinergic agent (e.g. Aclatonium Napadisilate) or Dopamine antagonist (e.g. Domperidone).

However, it is known that these known agents have the problems of insufficent therapeutic effects and side effects including diarrhea and extrapyramidal syndrome.

The gastrointestinal motility is controlled by both sympathetic and parasympathetic nervous systems. In the parasympathetic nervous system, acetylcholine is one of the most important neurotransmitters participating in the control of gastrointestinal motility. The release of acetylcholine from the nerves in the nerve plexus of gastrointestinal tract may induce the contraction of gastrointestinal tract. Accordingly, the accelerated release of acetylcholine from the nerve plexus of gastrointestinal tract results in sthenia of gastrointestinal motility.

Recently, a 5-$HT_4$ receptor was found in gastrointestinal tract. The 5-$HT_4$ receptor was reported to control the release of acetylcholine in the gastrointestinal nerve [Trends in Pharmacological Science, Vol. 13, 141–145, (1992)]. Thus, compounds acting on the 5-$HT_4$ receptor in the gastrointestinal tract and promoting the release of acetylcholine may be a more effective gastrokinetic agent with less side effects.

On the other hand, WO 9303725 discloses that (1-butyl-4-piperidyl)methyl-1-methylindazole-3-carboxylate (Example 10) has a 5-$HT_4$ receptor antagonist activity, and is of potential use in the treatment of diseases derived from 5-HT, diarrhea of irritable bowel syndrome due to the 5-HT activated intestinal nerve, cardiovascular disorders and CNS disorders. U.S. Pat. No. 3,145,215 discloses that N-[2-(4-methyl-1-piperazinyl)ethyl]-1H-indazole-3-carboxamide has hypotensive activity. However, it is not reported that those compounds have 5-$HT_4$ receptor agonist activities and gastrointestinal prokinetic actions.

Aliment. Pharmacol. Ther., Vol. 6, 273–289, 1992 suggests that irritable bowel syndrome exists as two types, constipation-type and diarrhea-type irritable bowel syndromes and 5-$HT_4$ receptor agonists are useful in the treatment of constipation-type irritable bowel syndrome, while Medicinal Research Reviews, Vol. 13, 633–662, 1993 suggests that 5-$HT_4$ receptor antagonists are useful in the treatment of diarrhea-type irritable bowel syndrome.

WO 9312785 discloses that 5-$HT_4$ receptor antagonists and agonists are of potential use in the treatment of conditions associated with bladder hypersensitivity and a poorly functioning bladder.

By elucidation of new compounds having a 5-$HT_4$ receptor agonist activity, it has been demanded to develop a medicine based on such a mechanism of action that acts on the 5-$HT_4$ receptor controlling the release of acetylcholine in the gastrointestinal nerve to promote the release of acetylcholine from the nerves in the nerve plexus of gastrointestinal tract, resulting in sthenia of a gastrointestinal motion, i.e., a 5-$HT_4$ receptor agonist.

DISCLOSURE OF INVENTION

As a result of our zealous search to solve such problems, we have found that the monocyclic amines, i.e., 4-piperidyl derivatives, 2-(4-piperidyl)ethyl derivatives, 2-(1-piperazinyl)ethyl derivatives, 2-(4-piperidylidene)-ethyl derivatives and 5-octahydroazocinyl derivatives have a prominent 5-$HT_4$ receptor agonist activity, and exhibit a gastrointestinal prokinetic action, which are effective for the treatment of the abnormality in function of a gastrointestinal motility by various causes such as chronic gastritis, gastrectomy, peptic ulcer, diabetes mellitus, scleroderma, and digestive tract diseases such as reflux esophagitis, irritable bowel syndrome with constipation as a chief complaint and spurious ileus.

The present invention provides an indazole derivative having a monocyclic amine, represented by formula

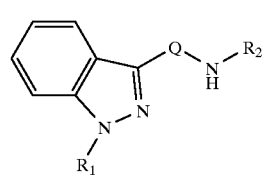

(I)

wherein $R_1$ is a hydrogen atom, a $C_1$–$C_6$ alkyl group, a $C_3$–$C_5$ alkenyl group or a $C_3$–$C_6$ cycloalkyl group, Q is a carbonyl group, a thiocarbonyl group or a methylene group, $R_2$ represents a group of formula (II), (III), (IV) or (V)

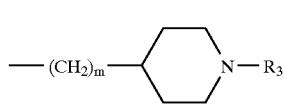

(II)

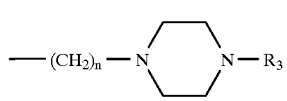

(III)

-continued

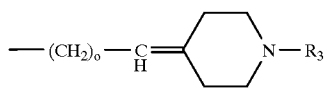 (IV)

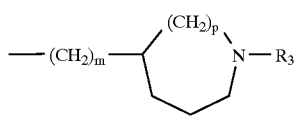 (V)

wherein $R_3$ is a $C_1$–$C_6$ alkyl group, a $C_3$–$C_6$ alkenyl group or a benzyl group, of which a phenyl ring may be substituted by the same or different halogen atom or methoxy group, m is 0–2, n is 2 or 3, o is 1 or 2, p is 2–4, and a pharmaceutically acceptable salt thereof.

In formula (I) for the indazole derivative having a monocyclic amine of the present invention, examples of the $C_1$–$C_6$ alkyl group represented by $R_1$ include methyl, ethyl, n-propyl, isopropyl, n-butyl, isobutyl, sec-butyl, (S)-sec-butyl, (R)- sec-butyl, tert-butyl, pentyl, isopentyl, 2-pentyl, 3-pentyl, neo-pentyl, tert-pentyl, hexyl and the like. Examples of the $C_3$–$C_6$ alkenyl group include allyl, 2-butenyl, 3-butenyl, 2-methyl-2-propenyl, 1-methyl-2-propenyl, 3-methyl-2-butenyl and the like. Examples of the $C_3$–$C_6$ cycloalkyl group include cyclopropyl, cyclobutyl, cyclopentyl, cyclohexyl and the like. Examples of the $C_1$–$C_6$ alkyl group represented by $R_3$ include methyl, ethyl, propyl, isopropyl, butyl, isobutyl, sec-butyl, tert-butyl, pentyl, isopentyl, 2-pentyl, 3-pentyl, neo-pentyl, tert-pentyl, hexyl and the like. Examples of the $C_3$–$C_6$ alkenyl group include allyl, 2-butenyl, 3-butenyl, 2-methyl-2-propenyl, 1-methyl-2-propenyl, 3-methyl-2-butenyl and the like. Examples of the benzyl group and mono- or di-substituted benzyl group include benzyl, o-fluorobenzyl, m-fluorobenzyl, p-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, o-chlorobenzyl, m-chlorobenzyl, p-chlorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, o-bromobenzyl, m-bromobenzyl, p-bromobenzyl, 2,3-dibromobenzyl, 2,4-dibromobenzyl, 2,5-dibromobenzyl, 2,6-dibromobenzyl, 3,4-dibromobenzyl, 3,5-dibromobenzyl, o-iodobenzyl, m-iodobenzyl, p-iodobenzyl, o-methoxybenzyl, m-methoxybenzyl, p-methoxybenzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl and the like.

The compounds of formula (I) according to the present invention can be prepared by various processes which will be explained below.

The compounds of formula (I')

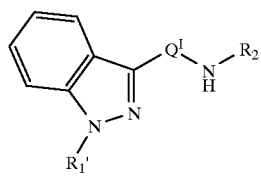 (I')

wherein
$R_1'$ is a $C_1$–$C_6$ alkyl group or a $C_3$–$C_6$ alkenyl group, $Q^1$ is a carbonyl group, $R_2$ represents a group having each of formulae (II)–(V)

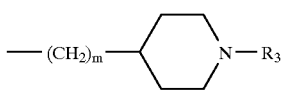 (II)

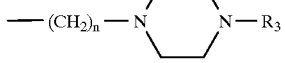 (III)

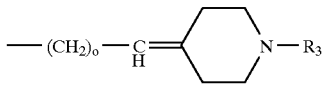 (IV)

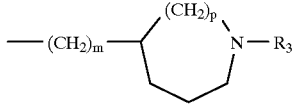 (V)

wherein $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, m is 0–2, n is 2 or 3, o is 1 or 2 and p is 2–4, can be prepared by reacting an indazole-3-carboxylic acid derivative of formula (VI)

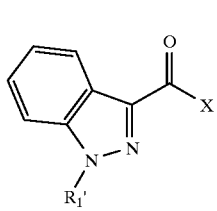 (VI)

wherein $R_1'$ is a $C_1$–$C_6$ alkyl group or a $C_3$–$C_6$ alkenyl group and X is OH, with an amine derivative having each of formulae (VII)–(X)

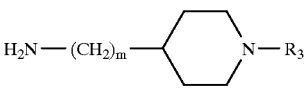 (VII)

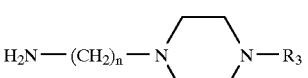 (VIII)

 (IX)

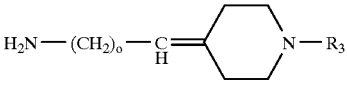

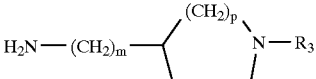 (X)

wherein $R_3$, m, n, o and p have the meanings as defined above, in the presence of a condensing agent such as carbodiimide derivatives or dialkylphosphorocyanidate derivatives.

Alternatively, the compounds of formula (I′) can be prepared by reacting an indazole-3-carboxylic acid derivative of formula (VI)

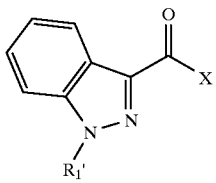

(VI)

wherein $R_1'$ is a $C_1$–$C_6$ alkyl group or a $C_3$–$C_6$ alkenyl group and X is a halogen atom or $R_4COO$ wherein $R_4$ is an alkyl group such as methyl or a haloalkyl group such as trifluoromethyl, or its reactive derivative with an amine derivative having each of formulae (VII)–(X)

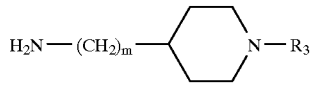

(VII)

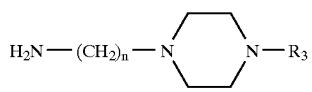

(VIII)

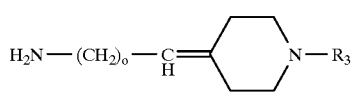

(IX)

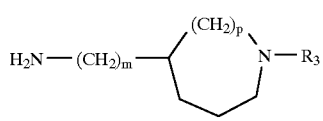

(X)

wherein $R_3$, m, n, o and p have the meanings as defined above, in the presence of a base.

The compounds of formula (I″)

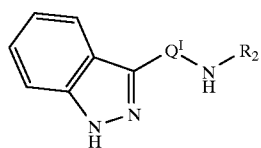

(I″)

wherein $Q_I$ is a carbonyl group, $R_2$ represents a group having each of formulae (II)–(V)

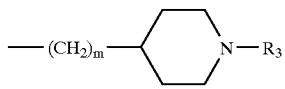

(II)

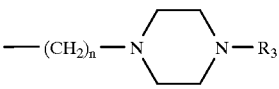

(III)

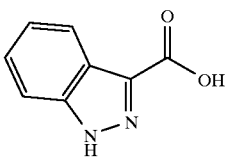

(IV)

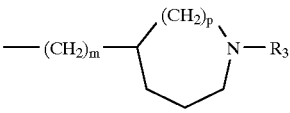

(V)

wherein $R_3$, m, n, o and p have the meanings as defined above can be prepared by reacting an indazole-3-carboxylic acid of formula (VI′)

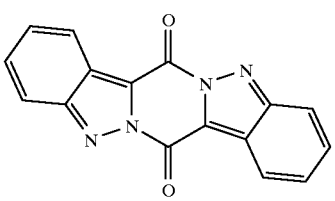

(VI′)

or its dimer, i.e., a diindazolo[2,3-a][2′, 3′-d]pyrazine-7,14-dione of formula (XI)

(XI)

with an amine derivative having each of formulae (VII)–(X)

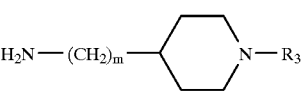

(VII)

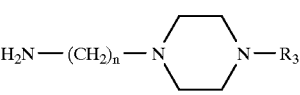

(VIII)

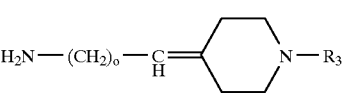

(IX)

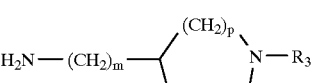

(X)

wherein $R_3$, m, n, o and p have the meanings as defined above.

The compounds of formula (I′)

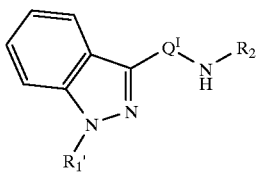

(I′)

wherein $R_1'$ is a $C_1$–$C_6$ alkyl group, a $C_3$–$C_6$ alkenyl group or a $C_3$–$C_6$ cycloalkyl group, $Q^I$ is a carbonyl group, and $R_2$ has the meaning as defined above, can be prepared by reacting the compounds of formula (I″) as obtained above with an alkylhalide or alkenylhalide of formula (XII)

$R_1'Y$ (XII)

wherein $R_1'$ is a $C_1$–$C_6$ alkyl group, a $C_3$–$C_6$ alkenyl group or a $C_3$–$C_5$ cycloalkyl group and Y is a halogen atom in the presence of a base, or by reacting the compound of formula (I″) with an alkylalcohol, an alkenylalcohol or a cycloalkylalcohol of formula (XII)

$R^{1''}Y$ (XII)

wherein $R_1$ is a $C_1$–$C_6$ alkyl group, a $C_3$–$C_6$ alkenyl group or a $C_3$–$C_6$ cycloalkyl group and Y is OH, and a di($C_1$–$C_6$) alkylazodicarboxylate in the presence of a tri-substituted phosphine.

The compounds of formula (I‴)

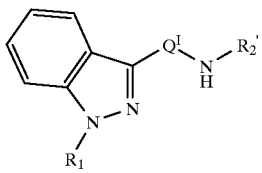

(I‴)

wherein $R_1$ is a hydrogen atom, a $C_1$–$C_6$ alkyl group, a $C_3$–$C_6$ alkenyl group or a $C_3$–$C_6$ cycloalkyl group, $Q^I$ is a carbonyl group and $R_2'$ represents a group having each of the following formulae (II′)–(V′)

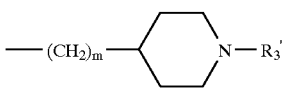

(II′)

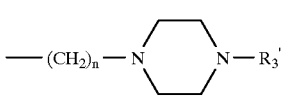

(III′)

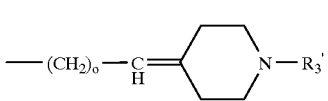

(IV′)

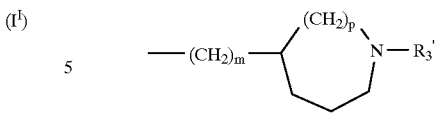

(V′)

wherein m, n, o and p have the meanings as defined above and $R_3'$ is a methyl group or a benzyl group, of which a phenyl ring may be substituted, are subjected to demetylation or debenzylation to give the compounds of formula (I″) wherein $R_3'$ is a hydrogen atom, which are then reacted with a compound of formula (XIII)

$R_3Z$ (XIII)

wherein $R_3$ is a $C_1$–$C_6$ alkyl group, a $C_3$–$C_6$ alkenyl group or a benzyl group, of which a phenyl ring may be mono- or di-substituted by the same or different halogen atom or methoxy group and Z is a halogen atom, thus preparing the compounds of formula (I′) wherein $R_3$ has the meaning as defined above.

The compounds of formula (I^{IV})

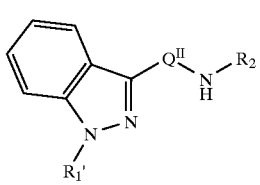

(I^{IV})

wherein $R_1'$ is a $C_1$–$C_6$ alkyl group, a $C_3$–$C_6$ alkenyl group or a $C_3$–$C_6$ cycloalkyl, $Q^{II}$ is a thiocarbonyl group and $R_2$ represents a group of formula (III)

—(CH_2)_n—N\underset{\underset{}{}}{⌒}N—R_3

(III)

wherein $R_3$ is a $C_1$–$C_6$ alkyl group, a $C_3$–$C_6$ alkenyl group or a benzyl group, of which a phenyl ring may be substituted by the same or different halogen atom or methoxy group and n is 2 or 3 can be prepared by reacting the compounds of formula (I′) wherein $Q^I$ is a carbonyl group and $R_1'$ and $R_2$ have the meanings as defined above, with [2,4-bis(4-methoxyphenyl)-1,3-dithia-2,4-diphosphetane-2,4-disulfide (called hereafter "Lawesson reagent") of formula (XIV)

(XIV)

[structure of Lawesson's reagent]

The compounds of formula ($I^V$)

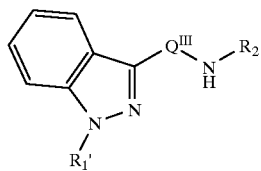
(IV)

wherein $R_1'$ is a $C_1$–$C_6$ alkyl group, a $C_3$–$C_6$ alkenyl group or a $C_3$–$C_6$ cycloalkyl group, $Q^{III}$ is a methylene group and $R_2$ represents the following formula (III)

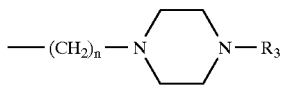
(III)

wherein $R_3$ is a $C_1$–$C_6$ alkyl group, a $C_3$–$C_6$ alkenyl group or a benzyl group, of which a phenyl ring may be mono- or di-substituted by the same or different halogen atom or methoxy group and n is 2 or 3 can be prepared by reacting the compounds of formula ($I'$) wherein $Q^I$ is a carbonyl group and $R_1'$ and $R_2$ have the meanings as defined above, with a reducing agent such as lithium aluminum hydride.

The above reactions are shown in Scheme 1.

(VI)

wherein $R_1'$ is a $C_1$–$C_6$ alkyl group or a $C_3$–$C_6$ alkenyl group and X is OH, or their derivatives with the amine derivatives having each of formulae (VII)–(X)

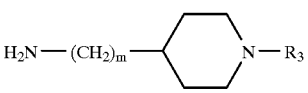
(VII)

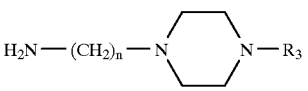
(VIII)

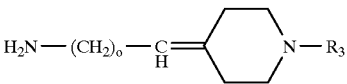
(IX)

Scheme 1

—$R_2'$—$R_3$ stands for a group represented by formulae (II)–(V).

Further, the processes for preparing the compounds of the invention will be illustrated in detail.

In the condensation of the indazole-3-carboxylic acids of formula (VI)

-continued

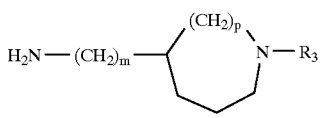
(X)

wherein $R_3$, m, n, o and p have the meanings as defined above, the reaction is carried out using 0.1–10 moles, preferably 0.5–2 moles of the indazole-3-carboxylic acids or their derivatives per mole of the amine derivatives, in the presence of 0.1–10 moles, preferably 0.5–2 moles of a condensing agent such as dialkyl phosphorocyanidate or carbodiimide derivative. In this reaction, 0.5–2 moles of 1-hydroxybenzotriazole (monohydrate) or N-hydroxysuccinimide may be used, if necessary. The reaction may be carried out at a temperature between the freezing point and the boiling point of the solvent, preferably at 0–40° C. Any solvent which is inactive in the reaction can be used, which can include hydrocarbons such as pentane, hexane, heptane, cyclohexane, petroleum ether, benzene and the like; halogenated hydrocarbons such as carbon tetrachloride, chloroform, methylene chloride and the like; ethers such as ethyl ether, THF, dioxane and the like; esters such as ethyl acetate and the like; acetone; DMF; DMSO; and nitromethane, but methylene chloride and DMF are preferred.

Examples of the indazole-3-carboxylic acids or their derivatives include the following:
indazole-3-carboxylic acid,
1-methylindazole-3-carboxylic acid,
1-ethylindazole-3-carboxylic acid,
1-propylindazole-3-carboxylic acid,
1-isopropylindazole-3-carboxylic acid,
1-butylindazole-3-carboxylic acid,
1-isobutylindazole-3-carboxylic acid,
1-(sec-butyl)indazole-3-carboxylic acid,
(S)-1-(sec-butyl)indazole-3-carboxylic acid,
(R)-1-(sec-butyl)indazole-3-carboxylic acid,
1-pentylindazole-3-carboxylic acid,
1-isopentylindazole-3-carboxylic acid,
1-(2-pentyl)indazole-3-carboxylic acid,
1-(3-pentyl)indazole-3-carboxylic acid,
1-(neo-pentyl)indazole-3-carboxylic acid,
1-allylindazole-3-carboxylic acid,
1-(2-butenyl)indazole-3-carboxylic acid,
1-(3-butenyl)indazole-3-carboxylic acid,
1-(2-methyl-2-propenyl)indazole-3-carboxylic acid,
1-(1-methyl-2-propenyl)indazole-3-carboxylic acid,
1-(3-methyl-2-butenyl)indazole-3-carboxylic acid,
1H-indazole-3-carboxylic acid and the like.

Examples of the amine derivatives include the following:
4-piperidylamine,
1-methyl-4-piperidylamine,
1-butyl-4-piperidylamine,
1-benzyl-4-piperidylamine,
(4-piperidyl)methylamine,
(1-methyl-4-piperidyl)methylamine,
(1-butyl-4-piperidyl)methylamine,
2-(1-methyl-4-piperidyl)ethylamine,
2-(1-butyl-4-piperidyl)ethylamine,
2-(4-methyl-1-piperazinyl)ethylamine,
2-(4-butyl-1-piperazinyl)ethylamine,
2-(4-p-fluorobenzyl-1-piperazinyl)ethylamine,
3-(4-butyl-1-piperazinyl)propylamine,
2-(1-methyl-4-piperidylidene)ethylamine,
2-(1-butyl-4-piperidylidene)ethylamine,
2-(1-p-fluorobenzyl-4-piperidylidene)ethylamine,
1-butyl-4-hexahydroazepinylamine,
1-butyl-5-octahydroazocinylamine,
1-butyl-5-octahydroazoninylamine and the like.

Examples of the dialkyl phosphorocyanidate derivatives include diethyl phosphorocyanidate and the like.

Examples of the carbodiimide derivatives can include dicyclohexylcarbodiimide, 1-ethyl-3-(3-dimethylaminopropyl)carbodiimide hydrochloride and the like.

In the reaction of the reactive derivatives of the indazole-3-carboxylic acids of formula (VI)

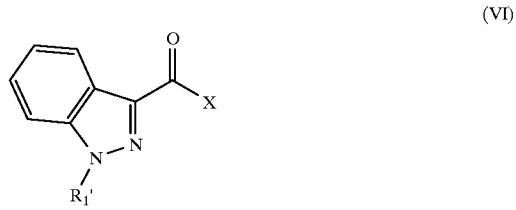
(VI)

wherein $R_1'$ is a $C_1$–$C_6$ alkyl group or a $C_3$–$C_6$ alkenyl group and X is a halogen atom or $R_4COO$ wherein $R_4$ is an alkyl group such as methyl or a haloalkyl group such as trifluoromethyl, or the dimer of indazole-3-carboxylic acid represented by formula (XI)

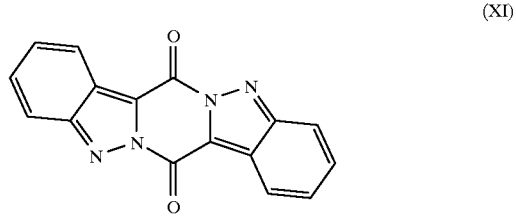
(XI)

with the amine derivatives having each of formulae (VII)–(X)

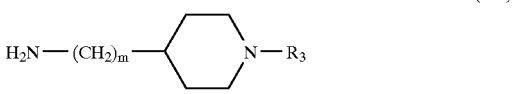
(VII)

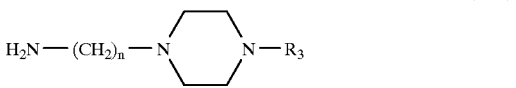
(VIII)

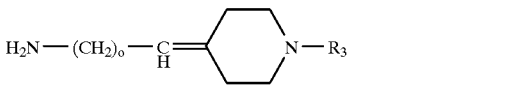
(IX)

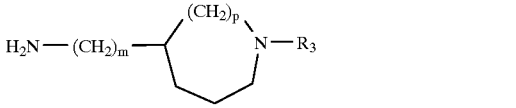
(X)

wherein $R_3$, m, n, o and p have the meanings as defined above, the reaction is carried out by using 0.1–10 moles, preferably 0.25–2 moles of the reactive derivatives of the indazole-3-carboxylic acids or the dimer of indazole-3-carboxylic acid per mole of the amine derivatives. The reaction may be carried out at a temperature between the freezing point and the boiling point of the solvent, preferably at 0–40° C. Any solvent which is inactive in the reaction can be used, which can include hydrocarbons such as pentane, hexane, heptane, cyclohexane, petroleum ether, benzene and the like; halogenated hydrocarbons such as carbon tetrachloride, chloroform, methlene chloride and the like; ethers such as diethyl ether, THF, dioxane and the like; esters such as ethyl acetate and the like; acetone; DMF, nitromethane; DMSO; HMPA; pyridine and the like, but DMF and DMSO are preferred. In this reaction, bases such as dimethylaminopyridine, triethylamine, pyridine, potassium carbonate, sodium carbonate and the like may be used, if necessary.

Examples of the reactive derivatives of indazole-3-carboxylic acids include the following:
1-methylindazole-3-carbonyl chloride,
1-ethylindazole-3-carbonyl chloride,
1-propylindazole-3-carbonyl chloride,
1-isopropylindazole-3-carbonyl chloride
1-butylindazole-3-carbonyl chloride,
1-isobutylindazole-3-carbonyl chloride,
1-(sec-butyl)indazole-3-carbonyl chloride,
(S)-1-(sec-butyl)indazole-3-carbonyl chloride,
(R)-1-(sec-butyl)indazole-3-carbonyl chloride,
1-(n-pentyl)indazole-3-carbonyl chloride,
1-isopentylindazole-3-carbonyl chloride,
1-(2-pentyl)indazole-3-carbonyl chloride,
1-(3-pentyl)indazole-3-carbonyl chloride,
1-(neo-pentyl)indazole-3-carbonyl chloride,
1-allylindazole-3-carbonyl chloride,
1-(2-butenyl)indazole-3-carbonyl chloride,
1-(3-butenyl)indazole-3-carbonyl chloride,
1-(2-methyl-2-propenyl)indazole-3-carbonyl chloride,
1-(1-methyl-2-propenyl)indazole-3-carbonyl chloride,
1-(3-methyl-2-butenyl)indazole-3-carbonyl chloride,
diindazolo[2,3-a][2',3'-d]pyrazine-7,14-dione and the like.

In the reaction of the 1H-indazole-3-carboxamide derivatives of formula ($I^H$)

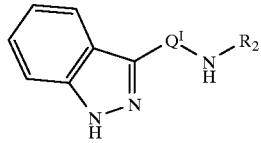

(I$^H$)

wherein $Q^I$ is a carbonyl group, $R_2$ has the meaning as defined above, with the halides of formula (XII)

$R_1'Y$ (XII)

wherein $R_1'$ is a $C_1$–$C_6$ alkyl group or a $C_3$–$C_6$ alkenyl group and Y is a halogen atom, the reaction is carried out by using 0.1–10 moles, preferably 0.5–3 moles of the halides per mole of the 1H-indazole-3-carboxamide derivatives in the presence of 0.1–10 moles, preferably 0.8–1.2 moles of a base. The reaction may be carried out at a temperature between the freezing point and the boiling point of the solvent, preferably at 0–40° C. Any solvent which is inactive in the reaction can be used, which can include hydrocarbons such as pentane, hexane, heptane, cyclohexane, petroleum ether, benzene and the like; ethers such as diethyl ether, THF, dioxane and the like; esters such as ethyl acetate and the like; DMF; DMSO and the like, but DMF is preferred.

Examples of the 1H-indazole-3-carboxamide derivatives include the following:

N-(4-piperidyl)-1H-indazole-3-carboxamide,
N-(1-methyl-4-piperidyl)-1H-indazole-3-carboxamide,
N-(1-butyl-4-piperidyl)-1H-indazole-3-carboxamide,
N-(1-benzyl-4-piperidyl)-1H-indazole-3-carboxamide,
N-(4-piperidyl)methyl-1H-indazole-3-carboxamide,
N-(1-methyl-4-piperidyl)methyl-1H-indazole-3-carboxamide,
N-(1-butyl-4-piperidyl)methyl-1H-indazole-3-carboxamide,
N-[2-(1-methyl-4-piperidyl)ethyl]-1H-indazole-3-carboxamide,
N-[2-(1-butyl-4-piperidyl)ethyl]-1H-indazole-3-carboxamide,
N-[2-(4-methyl-1-piperazinyl)ethyl]-1H-indazole-3-carboxamide,
N-[2-(4-butyl-1-piperazinyl)ethyl]-1H-indazole-3-carboxamide,
N-[2-(4-p-fluorobenzyl-1-piperazinyl)ethyl]-1H-indazole-3-carboxamide,
N-[3-(4-butyl-1-piperazinyl)propyl]-1H-indazole-3-carboxamide,
N-[2-(1-methyl-4-piperidylidene)ethyl]-1H-indazole-3-carboxamide,
N-[2-(1-butyl-4-piperidylidene)ethyl]-1H-indazole-3-carboxamide,
N-[2-(1-p-fluorobenzyl-4-piperidylidene)ethyl]-1H-indazole-3-carboxamide,
N-(1-butyl-4-hexahydroazepinyl)-1H-indazole-3-carboxamide,
N-(1-butyl-5-octahydroazocinyl)-1H-indazole-3-carboxamide and the like.

Examples of the halides include methyl iodide, ethyl bromide, ethyl iodide, propyl bromide, isopropyl chloride, isopropyl bromide, isopropyl iodide, butyl bromide, isobutyl chloride, isobutyl bromide, isobutyl iodide, sec-butyl chloride, sec-butyl bromide, sec-butyl iodide, (S)-sec-butyl chloride, (S)-sec-butyl bromide, (S)-sec-butyl iodide, (R)-sec-butyl chloride, (R)-sec-butyl bromide, (R)-sec-butyl iodide, pentyl bromide, isopentyl bromide, 2-pentyl bromide, 3-pentyl bromide, neo-pentyl bromide, allyl bromide, 2-butenyl bromide, 3-butenyl bromide, 2-methyl-2-propenyl bromide, 1-methyl-2-propenyl bromide, 3-methyl-2-butenyl bromide and the like.

Examples of the bases include sodium hydride, butyl lithium and the like.

In the reaction of the 1H-indazole-3-carboxamide derivatives of formula ($I^{II}$)

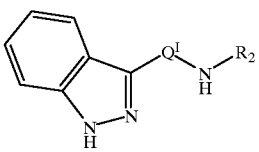

(I$^{II}$)

wherein $Q^I$ is a carbonyl group, $R_2$ has the meaning as defined above with the alcohols of formula (XII)

$R_1'Y$ (XII)

wherein $R_1'$ is a $C_1$–$C_6$ alkyl group, a $C_3$–$C_6$ alkenyl group or a $C_3$–$C_6$ cycloalkyl group and Y is OH, the reaction is carried out by using 0.5–2 moles, preferably 0.8–1.2 moles of the dialkylazodicarboxylate, 0.5–2 moles, preferably 0.8–1.2 moles of the tri-substituted phosphine and 0.5–2 moles, preferably 0.8–1.2 moles of the RX' per mole of the 1H-indazole-3-carboxamide derivatives. The reaction may be carried out at a temperature between the freezing point and the boiling point of the solvent, preferably at 0–100° C. Any solvents which is inactive in the reaction can be used and ethers such as diethyl ether, THF, dioxane and the like, and DMF are preferably used.

Examples of the alcohols include methanol, ethanol, propanol, isopropyl alcohol, butanol, isobutyl alcohol, sec-butyl alcohol, (S)-sec-butyl alcohol, (R)-sec-butyl alcohol, pentyl alcohol, isopentyl alcohol, 2-pentyl alcohol, 3-pentyl alcohol, neo-pentyl alcohol, allyl alcohol, cyclobutanol, cyclopentanol, cyclohexanol and the like.

Examples of the dialkylazodicarboxylates include diethylazodicarboxylate, diisopropylazodicarboxylate and the like.

Examples of the tri-substituted phosphines include triphenylphosphine, tributylphosphine and the like.

Debenzylation of the benzyl derivatives represented by formula ($I^{III}$)

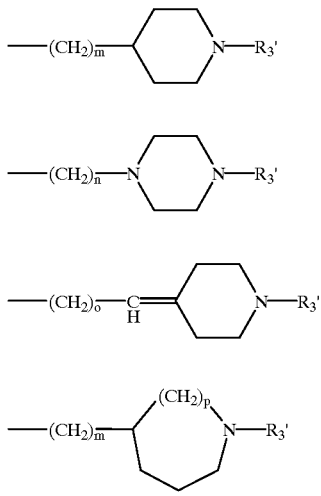

wherein $R_1$ is a hydrogen atom, a $C_1$–$C_6$ alkyl group, a $C_3$–$C_6$ alkenyl group or a $C_3$–$C_6$ cycloalkyl group, $Q^I$ is a carbonyl group and $R_2'$ represents a group having each of formulae ($II^I$)–($V^I$)

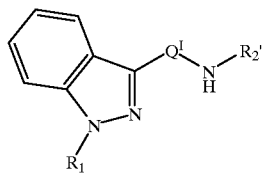

($II^I$)

($III^I$)

($IV^I$)

($V^I$)

wherein $R_3'$ is a benzyl group, m, n, o and p have the meanings as defined above, is carried out in the presence of a catalyst in a hydrogen atmosphere. The reaction is carried out at a pressure between ordinary pressure and 200 kg/cm², preferably between ordinary pressure and 100 kg/cm², at a temperature between the freezing point and the boiling point of the solvent, preferably at 0–100° C. The solvents which are preferably employed include alcohols such as methanol, ethanol, propanol, isopropyl alcohol and the like; water; and DMF.

Examples of the benzyl derivatives include the following:

N-(1-benzyl-4-piperidyl)-1-propylindazole-3-carboxamide,
N-(1-benzyl-4-piperidyl)methyl-1-propylindazole-3-carboxamide,
N-[2-(1-benzyl-4-piperidyl)ethyl]-1-propylindazole-3-carboxamide,
N-[2-(4-benzyl-1-piperazinyl)ethyl]-1-propylindazole-3-carboxamide,
N-[2-(4-benzyl-1-piperazinyl)ethyl]-1-sec-butylindazole-3-carboxamide,
N-[2-(4-benzyl-1-piperazinyl)ethyl]-1-(3-pentyl)indazole-3-carboxamide,
N-[2-(4-benzyl-1-piperazinyl)ethyl]-1H-indazole-3-carboxamide,
N-[2-(4-benzyl-1-piperazinyl)ethyl]-1-allylindazole-3-carboxamide,
N-[2-(1-benzyl-4-piperidylidene)ethyl]-1-propylindazole-3-carboxamide,
N-[2-(1-benzyl-4-piperidylidene)ethyl]-1H-indazole-3-carboxamide,
N-(1-benzyl-4-hexahydroazepinyl)-1-propylindazole-3-carboxamide,
N-(1-benzyl-5-octahydroazocinyl)-1-propylindazole-3-carboxamide,
N-(1-benzyl-5-octahydroazoninyl)-1-propylindazole-3-carboxamide and the like.

Examples of the catalysts include palladium-carbon, palladium hydroxide, Raney nickel and platinum (IV) oxide and the like.

Demethylation of the methyl derivatives represented by formula ($I^{III}$)

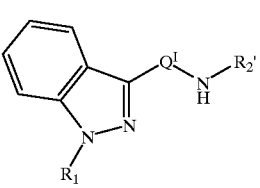

($I^{III}$)

wherein $R_1$ is a hydrogen atom, a $C_1$–$C_6$ alkyl group, a $C_3$–$C_6$ alkenyl group or a $C_3$–$C_6$ cycloalkyl, $Q_I$ is a carbonyl group and $R_2'$ represents a group having each of formulae ($II^I$)–($V^I$)

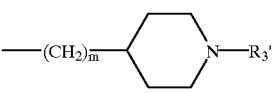

($II^I$)

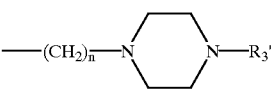

($III^I$)

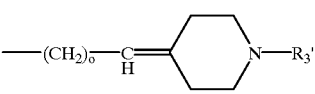

($IV^I$)

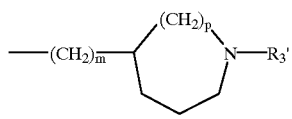
(V<sup>I</sup>)

wherein R$_3$' is a methyl group, m, n, o and p have the meanings as defined above, is carried out at a temperature of 0° to 200° C., preferably between room temperature and 120° C. in α-chloroethyl chloroformate.

Examples of the methyl derivatives include the following;
N-(1-methyl-4-piperidyl)-1-propylindazole-3-carboxamide,
N-(1-methyl-4-piperidyl)methyl-1-propylindazole-3-carboxamide,
N-[2-(1-methyl-4-piperidyl)ethyl]-1-propylindazole-3-carboxamide,
N-[2-(4-methyl-1-piperazinyl)ethyl]-1-propylindazole-3-carboxamide,
N-[2-(4-methyl-1-piperazinyl)ethyl]-1-sec-butylindazole-3-carboxamide,
N-[2-(4-methyl-1-piperazinyl)ethyl]-1-(3-pentyl)indazole-3-carboxamide,
N-[2-(4-methyl-1-piperazinyl)ethyl]-1H-indazole-3-carboxamide,
N-[2-(4-methyl-1-piperazinyl)ethyl]-1-allylindazole-3-carboxamide,
N-[2-(1-methyl-4-piperidylidene)ethyl]-1-propylindazole-3-carboxamide,
N-[2-(1-methyl-4-piperidylidene)ethyl]-1H-indazole-3-carboxamide,
N-(1-methyl-4-hexahydroazepinyl)-1-propylindazole-3-carboxamide,
N-(1-methyl-5-octahydroazocinyl)-1-propylindazole-3-carboxamide,
N-(1-methyl-5-octahydroazoninyl)-1-propylindazole-3-carboxamide and the like.

The reaction of the compounds of formula (I$^{IV}$) with the halides of formula (XIII)

R$_3$Z  (XIII)

wherein R$_3$ is a C$_1$–C$_6$ alkyl group, a C$_3$–C$_6$ alkenyl group or a benzyl group, of which a phenyl ring may be mono- or di-substituted by the same or different halogen atom or methoxy group, Z is a halogen atom can introduce the R$_3$ group as defined above into the demethylated or debenzylated derivatives of formula (I$^{VI}$)

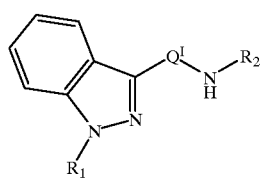
(I$^{VI}$)

wherein R$_1$ is a hydrogen atom, a C$_1$–C$_6$ alkyl group, a C$_3$–C$_6$ alkenyl group or a C$_3$–C$_6$ cycloalkyl, Q$^I$ is a carbonyl group and R$_2$ represents a group having each of formulae (II$^{II}$)–(V$^{II}$)

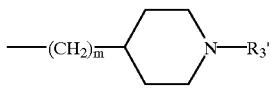
(II$^{II}$)

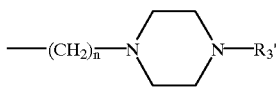
(III$^{II}$)

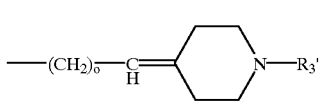
(IV$^{II}$)

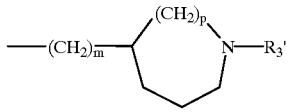
(V$^{II}$)

wherein R$^{3'}$ is a hydrogen atom, m, n, o and p have the meanings as defined above. The reaction is carried out at a temperature of 0–200° C., preferably between room temperature and 130° C. Any solvent which is inactive in the reaction can be used, which include alcohols such as methanol, ethanol, propanol, isopropyl alcohol, ethylene glycol and the like; chloroform, methylene chloride, DMF, acetonitrile, acetone, DMSO, HMPA and DMI. The reaction is also carried out, if necessary, in the presence of bases such as dimetylaminopyridine, triethylamine, pyridine, potassium carbonate, sodium carbonate and the like or fluorine-compounds such as potassium fluoride-cellite, lithium fluoride, sodium fluoride, cesium fluoride, rubidium fluoride and the like. Further, in case of using fluorine-compounds, crown ethers such as 18-crown-6, 15-crown-5 and the like may be used.

Alternatively, the introduction of the methyl group into the above-mentioned debenzylated derivatives may be achieved by performing the reaction under the condition from room temperature to reflux-heating in formic acid-formaldehyde.

Examples of the demethylated or debenzylated derivatives include the following:
N-(4-piperidyl)-1-propylindazole-3-carboxamide,
N-(4-piperidyl)methyl-1-propylindazole-3-carboxamide,
N-[2-(4-piperidyl)ethyl]-1-propylindazole-3-carboxamide,
N-[2-(1-piperazinyl)ethyl]-1-propylindazole-3-carboxamide,
N-[2-(1-piperazinyl)ethyl]-1-sec-butylindazole-3-carboxamide,
N-[2-(1-piperazinyl)ethyl]-1-(3-pentyl)indazole-3-carboxamide,
N-[2-(1-piperazinyl)ethyl]-1H-indazole-3-carboxamide,
N-[2-(1-piperazinyl)ethyl]-1-allylindazole-3-carboxamide,
N-[2-(-4-piperidylidene)ethyl]-1-propylindazole-3-carboxamide,
N-[2-(4-piperidylidene)ethyl]-1H-indazole-3-carboxamide,
N-(4-hexahydroazepinyl)-1-propylindazole-3-carboxamide,
N-(5-octahydroazocinyl)-1-propylindazole-3-carboxamide,
N-(5-octahydroazoninyl)-1-propylindazole-3-carboxamide and the like.

Examples of the halides include methyl iodide, ethyl bromide, ethyl iodide, propyl bromide, isopropyl chloride, isopropyl bromide, isopropyl iodide, butyl bromide, isobutyl chloride, isobutyl bromide, isobutyl iodide, sec-butyl chloride, sec-butyl bromide, sec-butyl iodide, (S)-sec-butyl chloride, (S)-sec-butyl bromide, (S)-sec-butyl iodide, (R)-sec-butyl chloride, (R)-sec-butyl bromide, (R)-sec-butyl iodide, pentyl bromide, isopentyl bromide, 2-pentyl bromide, 3-pentyl bromide, neo-pentyl bromide, allyl bromide, 2-butenyl bromide, 3-butenyl bromide, 2-methyl-2-propenyl bromide, 1-methyl-2-propenyl bromide, 3-methyl-2-butenyl bromide, p-fluorobenzyl chloride, p-chlorobenzyl chloride, p-bromobenzyl bromide, o-iodobenzyl chloride, p-methoxybenzyl chloride and the like.

The indazole-3-carboxamide derivatives represented by formula (I′)

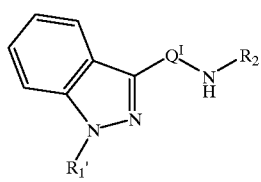

wherein $R_1'$ is a $C_1$–$C_6$ alkyl group, a $C_3$–$C_6$ alkenyl group or a $C_3$–$C_6$ cycloalkyl group, $Q^I$ is a carbonyl group, $R_2$ represents a group having each of formulae (II)–(V)

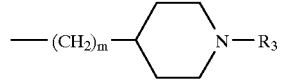

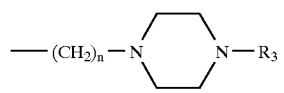

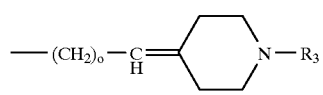

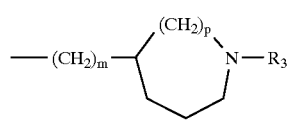

wherein $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, m, n, o and p have the meanings as defined above can be converted into the thioamide derivatives with 1–10 moles, preferably 1–2 moles of Lawesson's reagent represented by formula (XIV)

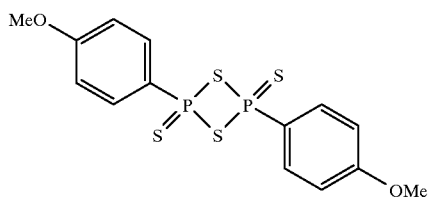

per mole of the indazole-3-carboxamide derivatives. The reaction may be carried out at a temperature between the freezing point and the boiling point of the solvent, preferably between room temperature and the boiling point of the solvent. Any solvent which is inactive in the reaction can be used, which include chloroform, methylene chloride, benzene, toluene, acetonitrile and the like.

The carbonyl group of the indazole-3-carboxamide derivatives represented by formula

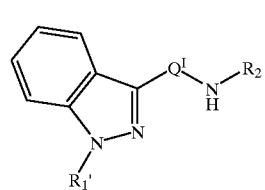

wherein
$R_1'$ is a $C_1$–$C_6$ alkyl group, a $C_3$–$C_6$ alkenyl group or a $C_3$–$C_6$ cycloalkyl group, $Q_I$ is a carbonyl group, $R_2$ represents a group having each of formulae (II)–(V)

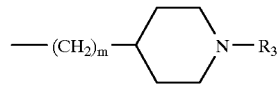

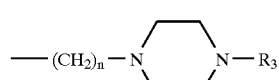

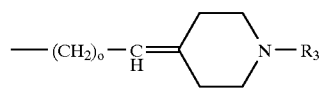

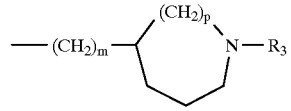

wherein $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, m, n, o and p have the meanings as defined above, can be converted into the methylene group with 1–10 moles, preferably 1–3 moles of a reducing agent such as lithium aluminum hydride, diborane and sodium bis(2-methoxyethoxy) aluminum hydride and the like per mole of the indazole-3-carboxamide derivatives. The reaction may be carried out at a temperature between the freezing point and the boiling point of the solvent, preferably between room temperature and the boiling point of the solvent. Any solvent which is inactive in the reaction can be used, which include ethers such as tetrahydrofuran, diethyl ether, dioxane and the like; chloroform; methylene chloride; benzene and toluene.

Amine derivatives of formula (VII)

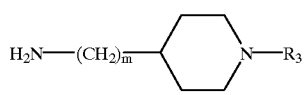

(VII)

wherein m is 0–2, $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, can be prepared by the processes shown in the following Scheme 2.

Amine derivatives of formula (VIII)

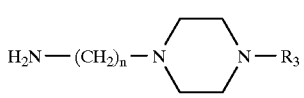

(VIII)

wherein n is 2 or 3, $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, can be prepared by the processes shown in the following Scheme 3.

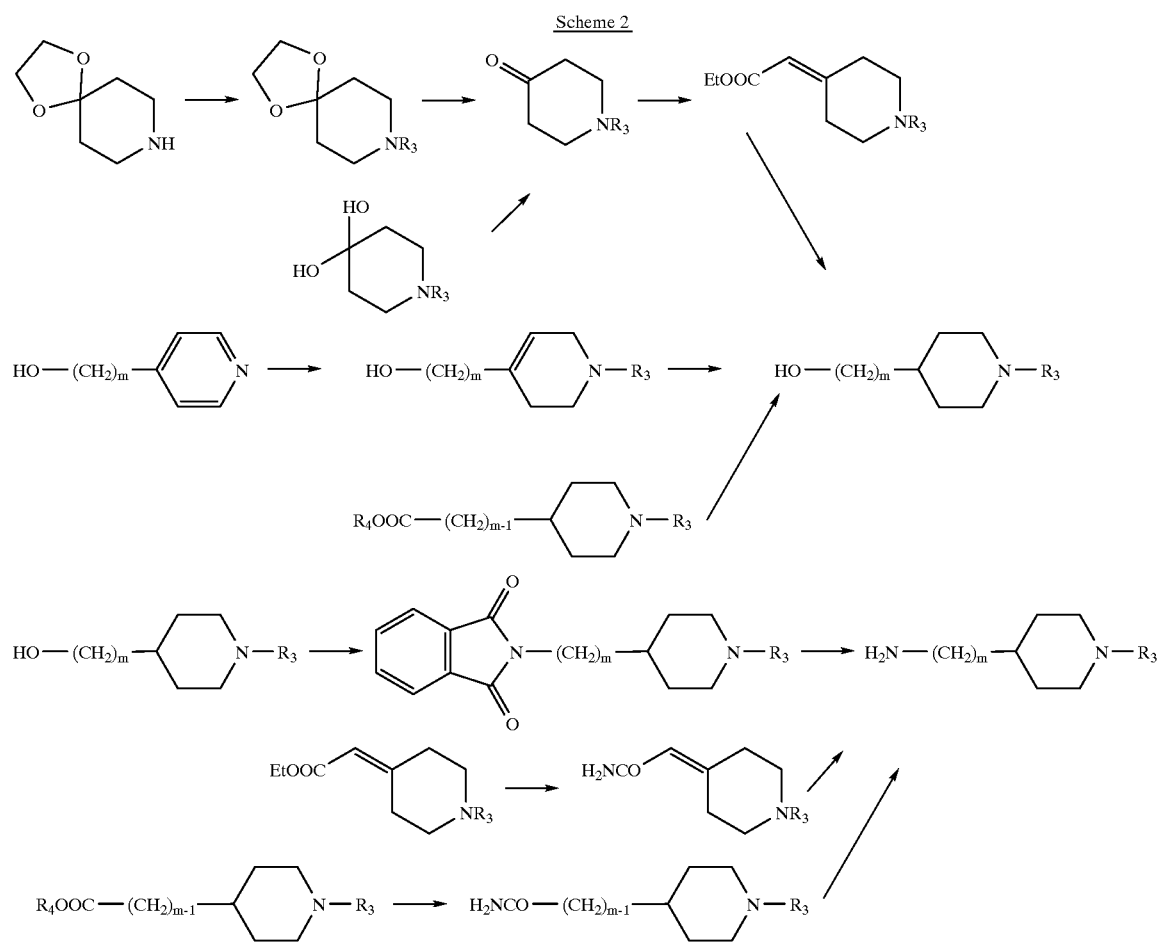

Scheme 2

$R_4$ represents an alkyl group, an arylalkyl group or an aryl group.

wherein $R_4$ represents an alkyl group, an arylalkyl group and an aryl group.

Scheme 3

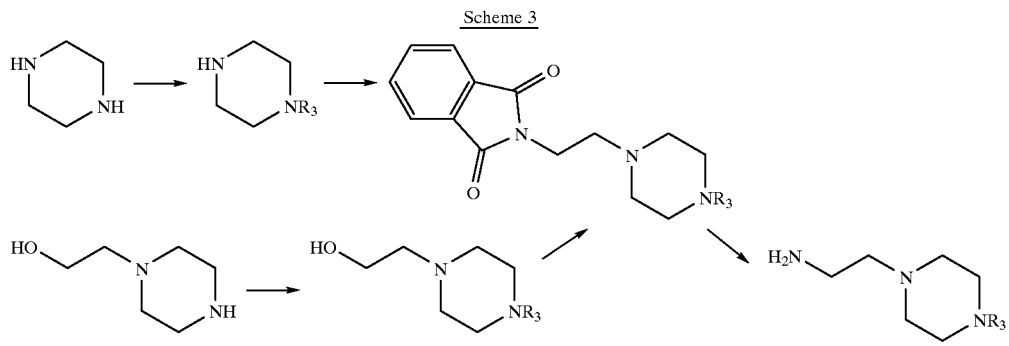

Amine derivatives of formula (IX)

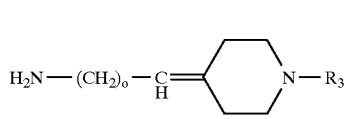
(IX)

wherein o is 1 or 2, $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, can be prepared by the processes shown in the following Scheme 4.

Amine derivatives of formula (X)

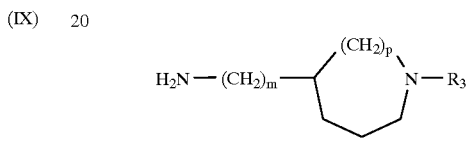
(X)

wherein p is 2–4, $R_3$ is a $C_1$–$C_6$ alkyl group, a $C_3$–$C_6$ alkenyl group or a benzyl group, of which a phenyl ring may be mono- or di-substituted by the same or different halogen atom or methoxy group, can be prepared by the processes Scheme 4

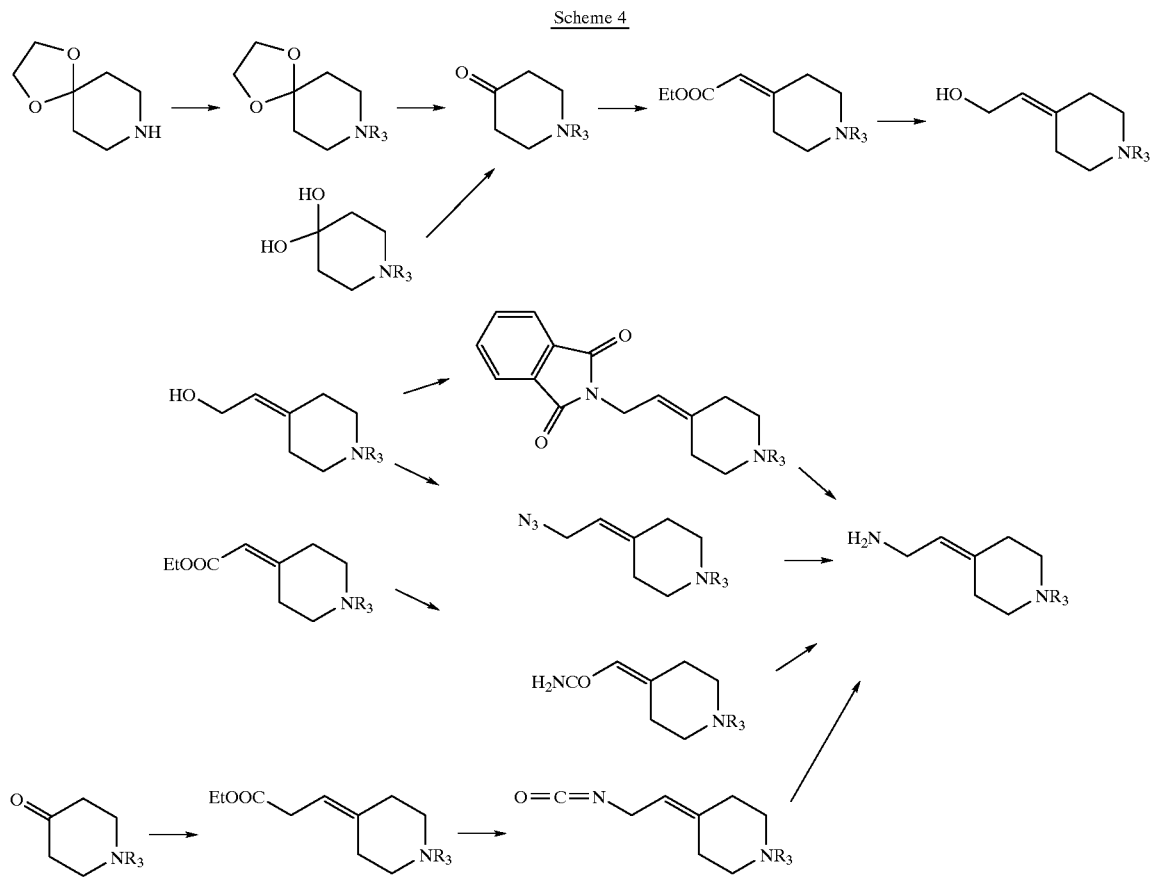

shown in the following Scheme 5.

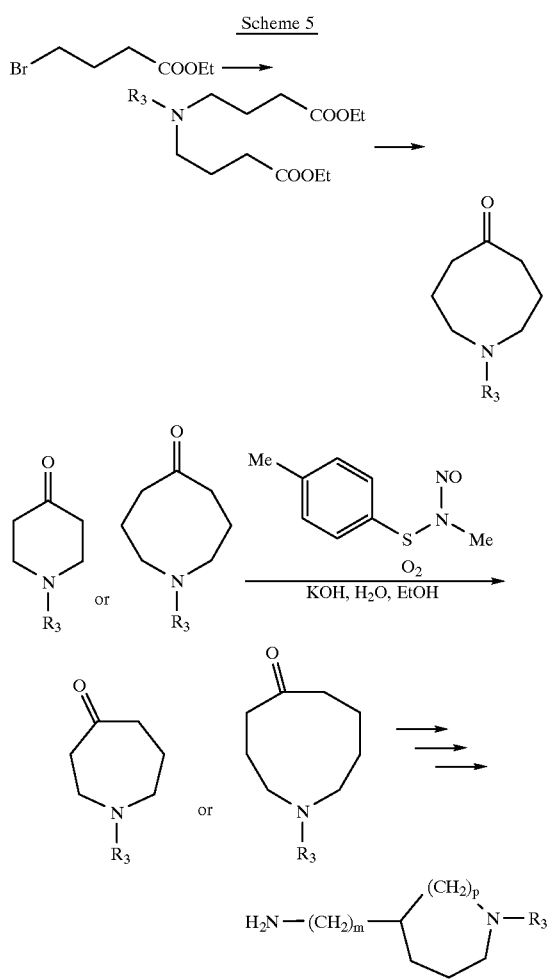

Examples of the thus prepared compounds of the present invention include the following:

N-(4-piperidyl)-1-propylindazole-3-carboxamide,
N-(1-methyl-4-piperidyl)-1-propylindazole-3-carboxamide,
N-(1-butyl-4-piperidyl)-1-propylindazole-3-carboxamide,
N-(1-benzyl-4-piperidyl)-1-propylindazole-3-carboxamide,
N-(4-piperidyl)methyl-1-propylindazole-3-carboxamide,
N-(1-methyl-4-piperidyl)methyl-1-propylindazole-3-carboxamide,
N-(1-butyl-4-piperidyl)methyl-1-propylindazole-3-carboxamide,
N-[2-(1-methyl-4-piperidyl)ethyl]-1-propylindazole-3-carboxamide,
N-[2-(1-butyl-4-piperidyl)ethyl]-1-propylindazole-3-carboxamide,
N-[2-(4-methyl-1-piperazinyl)ethyl]-1-propylindazole-3-carboxamide,
N-[2-(4-butyl-1-piperazinyl)ethyl]-1-prcpylindazole-3-carboxamide,
N-[2-(4-butyl-1-piperazinyl)ethyl]-1-sec-butylindazole-3-carboxamide,
N-[2-(4-butyl-1-piperazinyl)ethyl]-1-(3-pentyl)indazole-3-carboxamide,
N-[2-(4-p-fluorobenzyl-1-piperazinyl)ethyl]-1H-indazole-3-carboxamide,
N-[2-(4-p-fluorobenzyl-1-piperazinyl)ethyl]-1-propylindazole-3-carboxamide,
N-[2-(4-p-fluorobenzyl-1-piperazinyl)ethyl]-1-allylindazole-3-carboxamide,
N-[3-(4-butyl-1-piperazinyl)propyl]-1-proptindazole-3-carboxamide,
N-[2-(1-methyl-4-piperidylidene)ethyl]-1-propylindazole-3-carboxamide,
N-[2-(1-butyl-4-piperidylidene)ethyl]-1-propylindazole-3-carboxamide,
N-[2-(1-p-fluorobenzyl-4-piperidvlidene)ethyl]-1H-indazole-3-carboxamide,
N-[2-(1-p-fluorobenzyl-4-piperidylidene)ethyl]-1-propylindazole-3-carboxamide,
N-(1-butyl-4-hexahydroazepinyl)-1-propylindazole-3-carboxamide,
N-(1-butyl-5-octahydroazocinyl)-1-propylindazole-3-carboxamide,
N-(1-butyl-5-octahydroazoninyl)-1-propylindazole-3-carboxamide,
N-[2-(4-allyl-1-piperazinyl)ethyl]-1-n-propylindazole-3-carboxamide,
N-[2-(4-n-propyl-1-piperazinyl)ethyl]-1-n-propylindazole-3-carboxamide,
N-[2-(4-n-pentyl-1-piperazinyl)ethyl]-1-n-propylindazole-3-carboxamide,
N-[2-(4-p-methoxybenzyl-1-piperazinyl)ethyl]-1-n-propylindazole-3-carboxamide,
N-[2-(4-n-butyl-1-piperazinyl)ethyl]-1-ethylindazole-3-carboxamide,
N-[2-(4-n-butyl-1-piperazinyl)ethyl]-1-isopropylindazole-3-carboxamide,
N-[2-(4-n-butyl-1-piperazinyl)ethyl]-1-cyclopentylindazole-3-carboxamide,
N-[2-(4-n-butyl-1-piperazinyl)ethyl]-1-n-propylindazole-3-thiocarboxamide,
3-{N-[2-(4-n-butyl-1-piperazinyl)ethyl]aminomethyl}-1-n-propylindazole and the like.

The above compounds of the invention possess potent digestive tract prokinetic action via $5\text{-}HT_4$ receptors as shown in the following Examples, and are useful as a therapeutic agent for digestive tract diseases.

The compounds of formula (I) may be converted, if desired, to the corresponding acid addition salts with pharmaceutically acceptable acids, and the acid addition salts are included within the scope of this invention. They include, for examples, the salts with inorganic acids such as hydrochloric acid, hydrobromic acid, sulfuric acid, phosphoric acid and the like, or the salts with organic acids such as acetic acid, succinic acid, oxalic acid, malic acid, tartaric acid, fumaric acid, maleic acid, citric acid, malonic acid, lactic acid, methanesulfonic acid, p-toluenesulfonic acid, mandelic acid, suberic acid or the like.

The compounds of formula (I) can be formulated into the pharmaceutical preparations in various dosage forms. The preparations can be administered orally in the form of tablets, sugar-coated tablets, hard capsules, soft capsules and the liquid such as solutions, emulsions and suspensions. They are administered parenterally in the form of injections.

These preparations can be prepared by conventional methods employing conventional additives such as excipients, stabilizers, preservatives, solubilizers, wetting agents, emulsifiers, lubricants, sweetening agents, colorants, flavorings, isotonicity, buffers, antioxidants or the like.

Route and dosage for the administration of the present compounds are not specifically limited and are appropriately chosen depending upon the form of the pharmaceutical preparations, sex of the patient, severity of the disease and the like. Daily dosage of the active ingredient is 1 to 2000 mg. No adverse toxicological effects are indicated at any of the above dosage ranges.

This invention will be more fully illustrated by way of the following Preparation Examples with respect to the preparation of the intermediates of the present compounds, Examples with respect to the preparation of the present compounds and their pharmacological effects, and Pharmaceutical Examples with respect to the pharmaceutical preparation which comprises as an active ingredient the present compound. However, it is to be understood that the invention is not intended to be limited to the specific embodiments.

PREPARATION EXAMPLE 1

1-n-Butylpiperazine

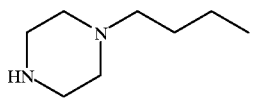

Anhydrous piperazine (19.5 g) was dissolved in ethanol (100 ml), and a solution of 1-bromobutane (24.8 g) in ethanol (50 ml) was added dropwise over a period of 20 minutes at room temperature. After stirring overnight, the reaction solution was filtered off with Celite, and the solvent was distilled off under reduced pressure. To the residue obtained was added a 40% aqueous solution of sodium hydroxide, and extracted with ether three times. The ether layer was dried over anhydrous magnesium sulfate, and the solvent was distilled off under reduced pressure. The residue was purified by silica gel column chromatography (methylene chloride:methanol:aqueous ammonia= 90:10:0.5) to give the title compound (7.53 g) as a yellow oily substance. Yield=29%.

$^1$H NMR(CDCl$_3$) δ 0.91(t, J=7 Hz, 3H), 1.27–1.36(m, 2H), 1.43–1.51(m, 2H), 2.01(bs, 1H), 2.31(t, J=8 Hz, 2H), 2.20–2.60(m, 4H), 2.90(t, J=5 Hz, 4H)

PREPARATION EXAMPLE 2

N-[3-(4-n-Butyl-1-piperazinyl)propyl]phthalimide

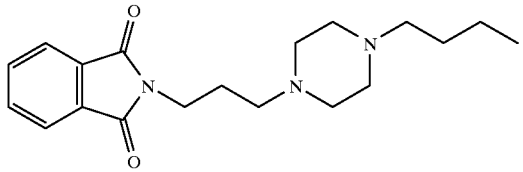

N-(3-Bromopropyl)phthalimide (15.1 g) was dissolved in acetonitrile (100 ml), and 1-n-butylpiperazine (5.33 g) obtained in Preparation Example 1 and 50% potassium fluoride-Celite (21.8 g) were added at room temperature. After stirring overnight, the reaction solution was filtered off with Celite, and the solvent was distilled off under reduced pressure. The residue obtained was purified by silica gel column chromatography (methylene chloride:methanol= 95:5) to give the title compound (9.83 g) as a yellow oily substance. Yield=80%.

$^1$H NMR(CDCl$_3$) δ 0.89(t, J=7 Hz, 3H), 1.23–1.33(m, 2H), 1.38–1.46(m, 2H), 1.82–1.89(m, 2H), 2.00–2.70(m, 8H), 2.24(t, J=8 Hz, 2H), 2.42(t, J=7 Hz, 2H), 3.76(t, J=7 Hz, 2H), 7.70–7.73(m, 2H), 7.82–7.85(m, 2H)

PREPARATION EXAMPLE 3

N-[2-(4-Methyl-1-piperazinyl)ethyl]phthalimide

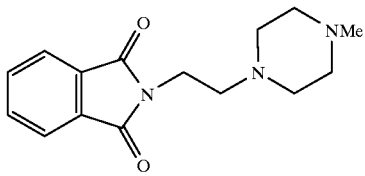

The title compound was synthesized by using N-(2-bromoethyl)phthalimide and 1-methylpiperazine according to the same process as in Preparation Example 2.

$^1$H NMR(CDCl$_3$) δ 2.26(s, 3H), 2.10–2.80(m, 8H), 2.64(t, J=7 Hz,2H), 3.81(t, J=7 Hz, 2H), 7.70–7.73(m, 2H), 7.82–7.85(m, 2H)

PREPARATION EXAMPLE 4

2-(4-n-Butyl-1-piperazinyl)ethanol

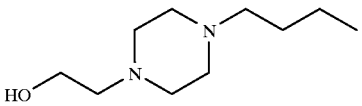

2-(1-Piperazinyl)ethanol (12.2 g) was dissolved in chloroform (60 ml), triethylamine (13.0 ml) and 1-bromobutane (14.1 g) were successively added at room temperature, and the mixture was stirred overnight. The reaction solution was successively washed with a 10 M aqueous solution of potassium hydroxide (15 ml), water (50 ml×2), saturated aqueous sodium chloride (50 ml), dried over anhydrous magnesium sulfate, and the solvent was distilled off under reduced pressure. The residue obtained was purified by silica gel column chromatography (methylene chloride:methanol:aqueous ammonia=90:10:0.5) to give the title compound (10.8 g) as a pale yellow oily substance. Yield=62%.

$^1$H NMR(CDCl$_3$) δ 0.91(t, J=7 Hz, 3H), 1.27–1.36(m, 2H), 1.43–1.51(m, 2H), 2.31–2.34(m, 2H), 2.30–2.60(m, 8H), 2.54(t, J=5 Hz,2H), 3.60(t, J=5 Hz, 2H)

PREPARATION EXAMPLE 5

2-(4-p-Fluorobenzyl-1-piperazinyl)ethanol

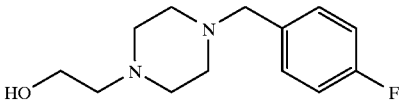

The title compound was synthesized by using 2-(1-piperazinyl)ethanol and p-fluorobenzyl chloride according to the same process as in Preparation Example 4.

$^1$H NMR(CDC$_{l3}$) δ 2.20–2.70(m, 8H), 2.54(t, J=5 Hz, 2H), 3.47(s, 2H), 3.60(t, J=5 Hz, 2H), 7.00(dd, J=8 Hz, 9 Hz, 2H), 7.28(dd, J=5 Hz, 9 Hz, 2H)

PREPARATION EXAMPLE 6

8-p-Fluorobenzyl-1,4-dioxa-8-azaspiro[4.5]decane

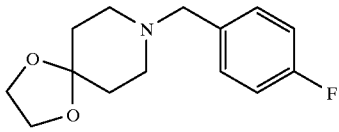

1,4-Dioxa-8-azaspiro[4.5]decane (29.9 g) was dissolved in chloroform (150 ml), triethylamine (32 ml) and p-fluorobenzyl chloride (27.5 ml) were successively added under ice-cooling, and the mixture was stirred overnight. The reaction solution was successively washed with a 20% aqueous solution of sodium hydroxide (150 ml×2) and water (150 ml), dried over anhydrous magnesium sulfate, and the solvent was distilled off under reduced pressure. The residue obtained was purified by silica gel column chromatography (chloroform:methanol=10:1) to give the title compound (49.4g) as a yellow oily substance. Yield=94%.

$^1$H NMR(CDC$_{13}$) δ 1.73(t, J=5 Hz, 4H), 2.50(bt, J=5 Hz, 4H), 3.48(s, 2H), 3.94(s, 4H), 6.96–7.01(m, 2H), 7.25–7.29 (m, 2H)

PREPARATION EXAMPLE 7

1-p-Fluorobenzyl-4-piperidone

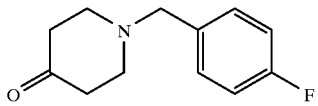

8-p-Fluorobenzyl-1,4-dioxa-8-azaspiro[4.5]decane (20.7 g) obtained in Preparation Example 6 was dissolved in 5N hydrochloric acid (200 ml), and the mixture was heated under reflux for 23 hours. The reaction solution was washed with chloroform (100 ml×3), made basic with potassium carbonate, and extracted with chloroform (100 ml×2,200 ml×1). The chloroform layer was dried over anhydrous magnesium sulfate, and the solvent was distilled off under reduced pressure to give the crude title compound (14.6 g) as a oily substance. Yield=85%. This compound was used for the subsequent reaction without purification.

$^1$H NMR(CDC$_{13}$) δ 2.45(t, J=6 Hz, 4H), 2.73(t, J=6 Hz, 4H), 3.58(s, 2H), 6.98–7.05(m, 2H), 7.28–7.34(m, 2H)

PREPARATION EXAMPLE 8

1-n-Butyl-4-piperidone

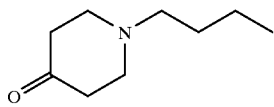

To a suspension of 4-piperidone hydrochloride monohydrate (20.6 g) and n-butylamine (25.0 g) in methylene chloride (300 ml) was added triethylamine (63 ml), and the mixture was stirred at room temperature for 12 hours. Methanol was further added to the reaction solution, and the solution was made uniform. To the solution were added water (7 ml) and anhydrous potassium carbonate (21.1 g), and the mixture was stirred for 30 minutes. The reaction solution was filtered off with Celite, and then the solvent was distilled off under reduced pressure. The residue obtained was purified by silica gel column chromatography (chloroform:methanol=10:1) to give the title compound (13.0 g) as a yellow oily substance. Yield=62%.

$^1$H NMR(CDC$_{13}$) δ 0.94(t, J=7 Hz, 3H), 1.36(sext, J=7 Hz, 2H), 1.47–1.53(m, 2H), 2.45(t, J=7 Hz, 2H), 2.46(t, J=6 Hz, 4H), 2.74(t, J=6 Hz, 4H)

PREPARATION EXAMPLE 9

Ethyl 1-p-fluorobenzyl-4-piperidylideneacetate

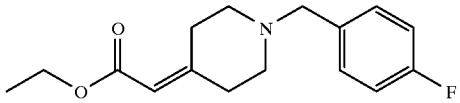

60% sodium hydride (0.87 g) was suspended in THF (30 ml), and ethyl diethylphosphonoacetate (5.5 ml) was added dropwise under ice-cooling. Then 1-p-fluorobenzyl-4-piperidone (3.76 g) obtained in Preparation Example 7 was added under ice-cooling, and the mixture was stirred for 3 hours. The reaction solution was poured into saturated aqueous sodium chloride (50 ml), and extracted with ethyl acetate (200 ml). The ethyl acetate layer was dried over anhydrous magnesium sulfate, and the solvent was distilled off under reduced pressure. The residue obtained was purified by silica gel column chromatography (ethyl acetate:hexane=1:4–2:3) to give the title compound (4.57 g) as a colorless oily substance. Yield=91%.

$^1$H NMR(CDCl$_3$) δ 1.27(t, J=7 Hz, 3H), 2.31(t, J=6 Hz, 2H), 2.49(t, J=5 Hz, 4H), 2.97(t, J=6 Hz, 2H), 3.47(s, 2H), 4.14(q, J=7 Hz, 2H), 5.63(s, 1H), 6.98–7.02(m, 2H), 7.26–7.30(m, 2H)

PREPARATION EXAMPLE 10

Ethyl 1-methyl-4-piperidylideneacetate

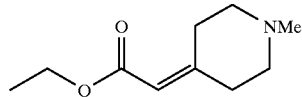

The title compound was synthesized by using 1-methyl-4-piperidone according to the same process as in Preparation Example 9.

$^1$H NMR(CDCl$_3$) δ 1.27(t, J=7 Hz, 3H), 2.29(s, 3H), 2.34(t, J=6 Hz, 2H), 2.45–2.50(m, 4H), 3.00(t, J=5 Hz, 2H), 4.14(q, J=7 Hz, 2H), 5.65(s, 1H)

PREPARATION EXAMPLE 11

Ethyl 1-n-butyl-4-piperidylideneacetate

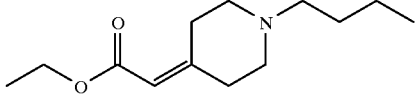

The title compound was synthesized by using 1-n-butyl-4-piperidone obtained in Preparation Example 8 according to the same process as in Preparation Example 9.

¹H NMR(CDCl₃) δ 0.92(t, J=7 Hz, 3H), 1.27(t, J=7 Hz, 3H), 1.29–1.35(m, 2H), 1.48(sept, J=8 Hz, 2H), 2.31–2.35 (m, 4H), 2.50(td, J=6 Hz, 9 Hz, 4H), 2.99(t, J=6 Hz, 2H), 4.14(q, J=7 Hz, 2H), 5.63(s,1H)

PREPARATION EXAMPLE 12

2-(1-p-Fluorobenzyl-4-piperidylidene)ethanol

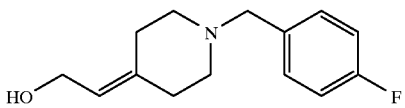

Ethyl 1-p-fluorobenzyl-4-piperidylideneacetate (2.97 g) obtained in Preparation Example 9 was dissolved in THF (30 ml), to which aluminum diisobutyl hydride (1.5M toluene solution, 18 ml) was added dropwise under ice-cooling, and the mixture was stirred for one hour. To the reaction solution were added aqueous ammonia (10 ml), a 10% aqueous solution of sodium hydroxide (20 ml) and Celite, and the mixture was stirred overnight at room temperature. The reaction solution was filtered off, extracted with chloroform (200 ml). The chloroform layer was washed with saturated aqueous sodium chloride (50 ml), dried over anhydrous magnesium sulfate, and the solvent was then distilled off under reduced pressure to give the title compound (2.57 g) as a pale yellow oily substance. This compound was used for the subsequent reaction without purification.

¹H NMR(CDCl₃) δ 2.23(t, J=5 Hz, 2H), 2.30(t, J=6 Hz, 2H), 2.40–2.45(m, 4H), 3.46(s, 2H), 4.13(d, J=7 Hz, 2H), 5.41(t, J=7 Hz, 1H), 6.97–7.01(m, 2H), 7.26–7.29(m, 2H)

PREPARATION EXAMPLE 13

2-(1-Methyl-4-piperidylidene)ethanol

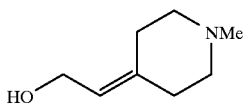

The title compound was synthesized by using ethyl 1-methyl-4-piperidylideneacetate obtained in Preparation Example 10 according to the same process as in Preparation Example 12.

¹H NMR(CDCl₃) δ 2.26(t, J=6 Hz, 2H), 2.33(t, J=6 Hz, 2H), 2.38–2.43(m, 4H), 4.14(d, J=7 Hz, 2H), 5.42(t, J=7 Hz, 1H)

PREPARATION EXAMPLE 14

2-(1-Methyl-4-piperidyl)ethanol

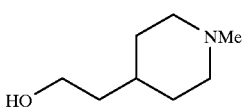

To a solution of 2-(1-methyl-4-piperidylidene)-ethanol (4.50 g) obtained in Preparation Example 13 in ethanol (50 ml) was added platinum (IV) oxide (0.10 g), and the mixture was shaken at room temperature under hydrogen atmosphere at 2.1 kg cm² for 5 hours. The reaction solution was filtered off with Celite, and the solvent was distilled off under reduced pressure to give the title compound (4.73 g). This compound was used for the subsequent reaction without purification.

¹H NMR(CDCl₃) δ 1.23–1.33(m, 2H), 1.36–1,46(m, 1H), 1.52(q, J=7 Hz, 2H), 1.69(d, J=13 Hz, 2H), 1.91(dt, J=2 Hz, 12 Hz, 2H), 2.18(s, 1H), 2.25(s, 3H), 2.83(d, J=12 Hz, 2H), 3.68(t, J=7 Hz, 2H)

PREPARATION EXAMPLE 15

2-(1-n-Butyl-4-piperidylidene)ethanol

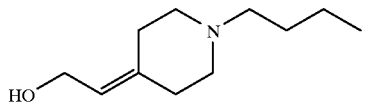

The title compound was synthesized by using ethyl 1-n-butyl-4-piperidylideneacetate obtained in Preparation Example 11 according to the same process as in Preparation Example 12.

¹H NMR(CDCl₃) δ 0.91(t, J=7 Hz, 3H), 1.25–1.36(m, 2H), 1.44–1.52(m, 2H), 2.25(t, J=6 Hz, 2H), 2.30–2.37(m, 4H), 2.42–2.47(m,4H), 4.14(d, J=7 Hz, 2H), 5.41(t, J=7 Hz, 1H)

PREPARATION EXAMPLE 16

2-(1-n-Butyl-4-piperidyl)ethanol

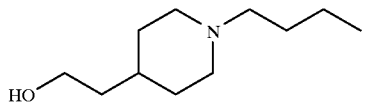

A suspension of lithium aluminum hydride (0.96 g) in THF (90 ml) was ice-cooled, to which was added dropwise a solution of ethyl 1-n-butyl-4-piperidylideneacetate (3.40 g) obtained in Preparation Example 11 in THF (60 ml) over a period of 10 minutes with stirring. The mixture was stirred under ice-cooling for 10 minutes, and then at room temperature for further 2 hours. To the reaction solution were successively added water (4 ml), a 15% aqueous solution of sodium hydroxide (4 ml), water (12 ml), and anhydrous magnesium sulfate, and the mixture was stirred at room temperature for 30 minutes. The reaction solution was filtered off with Celite, and the solvent was distilled off under reduced pressure. To a solution of the residue in ethanol (150 ml) was added platinum (IV) oxide (0.50 g), and the mixture was shaken at room temperature under hydrogen atmosphere at 2 kg/cm² for 11 hours. The reaction solution was filtered off with Celite, and the solvent was distilled off under reduced pressure to give the title compound (2.76 g) as a yellow oily substance. This compound was used for the subsequent reaction without purification.

PREPARATION EXAMPLE 17

(1-Methyl-1,2,5,6-tetrahydro-4-pyridyl)methanol

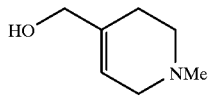

4-Pyridylmethanol (25.0 g) and methyl iodide (16 ml) were reacted at 120° C. in a sealed tube for 3 hours. The quaternary ammonium salt obtained was dissolved in 10% aqueous methanol (300 ml), and the solution was cooled to −78° C. Sodium borohydride (42.0 g) was added over a period of 2 hours with stirring. After completion of the reaction, the solvent was distilled off under reduced pressure. To the residue was added a 20% aqueous solution of sodium hydroxide, and extracted with chloroform. The chloroform layer was washed with saturated aqueous sodium chloride, dried over anhydrous potassium carbonate, and the solvent was distilled off under reduced pressure. The residue obtained was purified by silica gel column chromatography (chloroform:methanol:aqueous ammonia=90:10:1) to give the title compound (17.58 g) as a yellow oily substance. Yield=60%.

$^1$H NMR(CDCl$_3$) δ 2.14(s, 2H), 2.33(t, J=1 Hz, 3H), 2.58(dt, J=1 Hz, 6 Hz, 2H), 2.92(s, 2H), 3.95(s, 2H), 4.49(bs, 1H), 5.58(t, J=2 Hz, 1H)

PREPARATION EXAMPLE 18

(1-Methyl-4-piperidyl)methanol

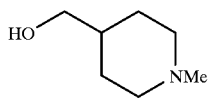

To a solution of (1-methyl-1,2,5,6-tetrahydro-4-pyridyl)methanol (17.6 g) obtained in Preparation Example 17 in ethanol (200 ml) was added platinum (IV) oxide (0.40 g), and the mixture was shaken at room temperature under hydrogen atmosphere at 2 kg/cm$^2$ for 5 hours. The reaction solution was filtered off with Celite, and the solvent was −distilled off under reduced pressure. The residue was purified by vacuum distillation to give the title compound (14.2g). Yield 80%.

b.p. 82–86:° C. (3 mmHg)$^1$H NMR(CDCl$_3$) δ 1.22–1.38 (m, 2H), 1.42–1.47(m, 1H), 1.75(bd, J=13 Hz, 2H), 1.93(bt, J=11 Hz, 2H), 2.26(s, 3H), 2.87(d, J=11 Hz, 2H), 3.46(dd, J=6 Hz, 11 Hz, 2H)

PREPARATION EXAMPLE 19

Ethyl 1-n-butylisonipecotate and 1-n-butylisonipecotic acid

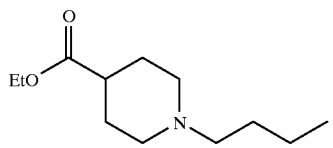

-continued

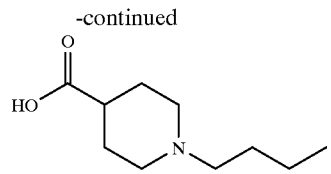

Ethyl isonipecotate (24.0 g) was dissolved in ethanol (200 ml), triethylamine (23 ml) and 1-bromobutane (18 ml) were added in turn at room temperature, and the mixture was stirred for 24 hours. Water (10 ml) and anhydrous potassium carbonate (30 g) were further added, and the mixture was stirred for 10 minutes. The reaction solution was filtered off with Celite, and the solvent was distilled off under reduced pressure. The residue was washed with saturated aqueous sodium chloride, then dried over anhydrous magnesium sulfate and the solvent was distilled off under reduced pressure. The residue was purified by vacuum distillation to give a mixture (16.9 g) of the title compounds. Yield=53%.

b.p. 110–115° C. (9 mmHg)

PREPARATION EXAMPLE 20

(1-n-Butyl-4-piperidyl)methanol

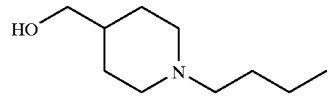

A suspension of lithium aluminum hydride (1.39 g) in THF (100 ml) was ice-cooled, to which was added dropwise a solution of a mixture (4.15 g) of ethyl 1-n-butylisonipecotate and 1-n-butylisonipecotic acid obtained in Preparation Example 19 in THF (100 ml) over a period of 15 minutes with stirring. The mixture was stirred under ice-cooling for 10 minutes, and then at room temperature for 30 minutes. To the reaction solution were successively added water (2 ml), a 15% aqueous solution of sodium hydroxide (2 ml), water (6 ml) and anhydrous magnesium sulfate, and the mixture was stirred at room temperature for 30 minutes. The reaction solution was filtered off with Celite, and the solvent was distilled off under reduced pressure to give the title compound (3.84 g). This compound was used for the subsequent reaction without purification.

$^1$H NMR(CDCl$_3$) δ 0.91(t, J=7 Hz, 3H), 1.30(sext, J=7 Hz, 2H), 1.37–1.54(m, 5H), 1.87(dt, J=2 Hz, 12 Hz, 2H), 2.29(t, J=8 Hz, 2H), 2.91(d, J=12 Hz, 2H), 3.68(dt, J=2 Hz, 6 Hz, 2H)

PREPARATION EXAMPLE 21

N-[2-(4-n-Butyl-1-piperazinyl)ethyl]phthalimide

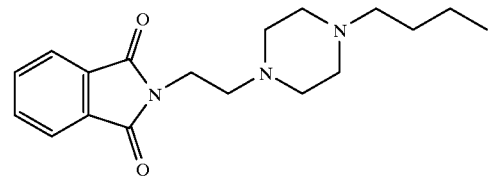

2-(4-n-Butyl-1-piperazinyl)ethanol (5.46 g) obtained in Preparation Example 4, triphenylphosphine (8.46 g) and phthalimide (4.74 g) were dissolved in THF (50 ml), and diisopropylazodicarboxylate (6.52 g) was added dropwise at room temperature. After stirring overnight, the reaction solution was distilled off under reduced pressure. The residue obtained was purified by silica gel column chromatography (methylene chloride:ethyl acetate=1:1) to give the title compound (6.64 g). Yield 72%.

$^1$H NMR(CDCl$_3$) δ 0.88(t, J=7 Hz, 3H), 1.25 1.31(m, 2H), 1.40–1.45(m, 2H), 2.20–2.80(m, 8H), 2.28(t, J=8 Hz, 2H), 2.62(t, J=7 Hz, 2H), 3.80(t, J=7 Hz, 2H), 7.68–7.71(m, 2H), 7.80–7.84(m, 2H)

PREPARATION EXAMPLE 22

N-[2-(4-p-Fluorobenzyl-1-piperazinyl)ethyl]phthalimide

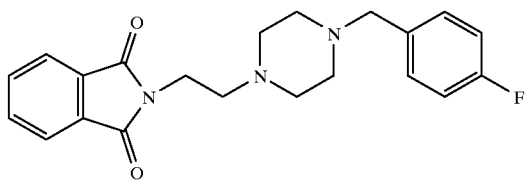

The title compound was synthesized by using 2-(4-p-fluorobenzyl-1-piperazinyl)ethanol obtained in Preparation Example 5 according to the same process as in Preparation Example 21.

$^1$H NMR(CDCl$_3$) δ 2.30–2.70(m, 8H), 2.63(t, J=7 Hz, 2H), 3.43(s, 2H), 3.81(t, J=7 Hz, 2H), 7.00(dd, J=8 Hz, 9 Hz, 2H), 7.25(dd, J=5 Hz, 9 Hz, 2H), 7.71(dd, J=3 Hz, 5 Hz, 2H), 7.84(dd, J=3 Hz, 9 Hz, 2H)

PREPARATION EXAMPLE 23

N-[2-(1-Methyl-4-piperidylidene)ethyl]phthalimide

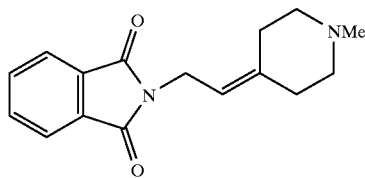

The title compound was synthesized by using 2-(1-methyl-4-piperidylidene)ethanol obtained in Preparation Example 13 according to the same process as in Preparation Example 21.

$^1$H NMR(CDCl$_3$) δ 2.23(t, J=6 Hz, 2H), 2.30(s, 3H), 2.41(t, J=6 Hz, 2H), 2.48(t, J=5 Hz, 2H), 2.54(t, J=5 Hz, 2H), 4.27(d, J=7 Hz,2H), 5.30(t, J=7 Hz, 1H), 7.69–7.73(m, 2H), 7.82–7.85(m, 2H)

PREPARATION EXAMPLE 24

N-[2-(1-n-Butyl-4-piperidylidene)ethyl]phthalimide

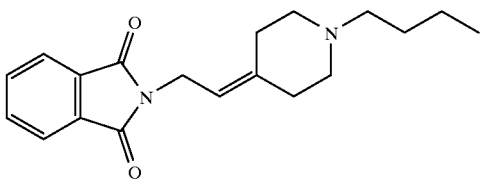

The title compound was synthesized by using 2-(1-n-butyl-4-piperidylidene)ethanol obtained in Preparation Example 15 according to the same process as in Preparation Example 21.

$^1$H NMR(CDCl$_3$) δ 0.91(t, J=8 Hz, 3H), 1.25–136(m, 2H), 1.47–1.55(m, 2H), 2.18–2.30(m, 2H), 2.30–2.44(m, 2H), 2.44–2.45(m,2H), 2.54–2.65(m, 2H), 4.27(d, J=7 Hz, 2H), 5.29(t, J=7 Hz, 1H), 7.69–7.72(m, 2H), 7.82–7.84(m, 2H)

PREPARATION EXAMPLE 25

N-[2-(1-p-Fluorobenzyl-4-piperidylidene)ethyl]phthalimide

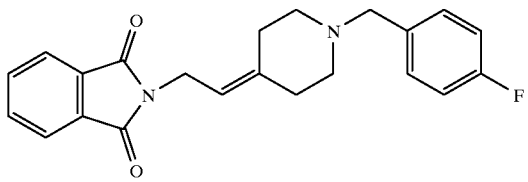

The title compound was synthesized by using 2-(1-p-fluorobenzyl-4-piperidylidene)ethanol obtained in Preparation Example 12 according to the same process as in Preparation Example 21.

$^1$H NMR(CDCl$_3$) δ 2.18(t, J=5 Hz, 2H), 2.39(t, J=6 Hz, 2H), 2.48(bs, 4H), 3.46(s, 2H), 4.26(d, J=7 Hz, 2H), 5.28(t, J=7 Hz, 1H), 6.99(t, J=8 Hz, 2H), 7.27(dd, J=5 Hz, 8 Hz, 2H), 7.70(dd, J=3 Hz, 5 Hz, 2H), 7.83(dd, J=3 Hz, 5 Hz, 2H)

PREPARATION EXAMPLE 26

N-(1-Methyl-4-piperidyl)methylphthalimide

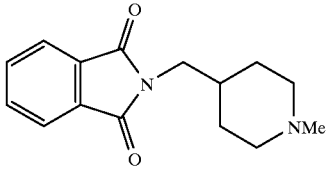

(1-Methyl-4-piperidyl)methanol (4.00 g) obtained in Preparation Example 18, triphenylphosphine (9.00 g) and phthalimide (5.04 g) were suspended in THF (40 ml), to which diethyl azocarboxylate (6.7 ml) was added dropwise at room temperature, and the mixture was stirred for 12 hours. The reaction solution was distilled off under reduced pressure. The residue was purified by silica gel column chromatography (methanol:ethyl acetate=1:10–methanol:chloroform=1:5) to give the title compound (6.34 g). Yield=79%.

¹H NMR(CDCl₃) δ 1.34–1.44(m, 2H), 1.67(d, J=13 Hz, 2H), 1.68–1.84(m, 1H), 1.87(dt, J=1 Hz, 12 Hz, 2H), 2.24(s. 3H), 2.83(d, J=12 Hz, 2H), 7.23–7.28(m, 2H), 7.83–7.85(m, 2H)

PREPARATION EXAMPLE 27

N-(1-n-Butyl-4-piperidyl)methylphthalimide

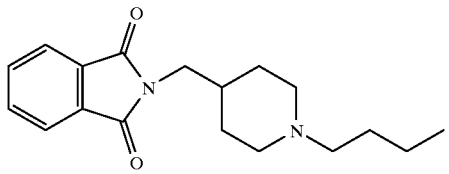

The title compound was synthesized by using (1-n-butyl-4-piperidyl)methanol obtained in Preparation Example 20 according to the same process as in Preparation Example 26.

¹H NMR(CDCl₃) δ 0.90(t, J=7 Hz, 3H), 1.29(sept, J=7 Hz, 2H), 1.35–1.44(m, 2H), 1.45(sept, J=8 Hz, 2H), 1.66(d, J=13 Hz, 2H), 1.74–1.82(m, 1H), 1.87(t, J=11 Hz, 2H), 2.29(t, J=8 Hz, 2H), 2.90(d, J=11 Hz, 2H), 3.60(d, J=7 Hz, 2H), 7.70–7.72(m, 2H), 7.83–7.85(m, 2H)

PREPARATION EXAMPLE 28

N-[2-(1-Methyl-4-piperidyl)ethyl]phthalimide

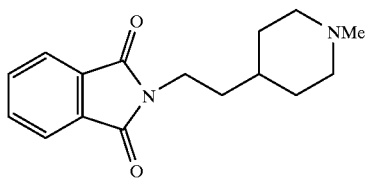

The title compound was synthesized by using 2-(1-methyl-4-piperidyl)ethanol obtained in Preparation Example 14 according to the same process as in Preparation Example 26.

¹H NMR(CDCl₃) δ 1.22–1.38(m, 3H), 1.62(q, J=7 Hz, 2H), 1.79(d, J=11 Hz, 2H), 1.91(dd, J=10 Hz, 11 Hz, 2H), 2.26(s, 3H), 2.87(d, J=11 Hz, 2H), 3.72(t, J=7 Hz, 2H), 7.71(d, J=5 Hz, 2H), 7.84(d, J=5 Hz, 2H)

PREPARATION EXAMPLE 29

N-[2-(1-n-Butyl-4-piperidyl)ethyl]phthalimide

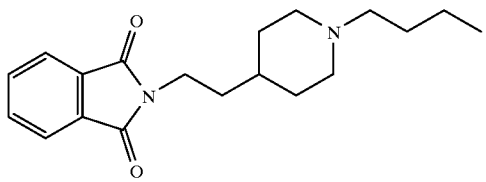

The title compound was synthesized by using 2-(1-n-butyl-4-piperidyl)ethanol obtained in Preparation Example 16 according to the same process as in Preparation Example 26.

¹H NMR(CDCl₃) δ 0.91(t, J=7 Hz, 3H), 1.25–1.35(m, 5H), 1.48(sept, J=7 Hz, 2H), 1.62(q, J=6 Hz, 2H), 1.78(d, J=10 Hz, 2H), 1.89(t, J=10 Hz, 2H), 2.30(t, J=8 Hz, 2H), 2.93(d, J=11 Hz, 2H), 3.72(t, J=7 Hz, 2H), 7.70–7.72(m, 2H), 7.83–7.85(m, 2H)

PREPARATION EXAMPLE 30

3-(4-n-Butyl-1-piperazinyl)propylamine

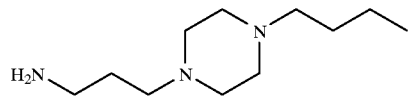

N-[3-(4-n-Butyl-1-piperazinyl)propyl]phthalimide (8.18 g) obtained in Preparation Example 2 was dissolved in methanol (80 ml), hydrazine monohydrate (1.86 g) was added at room temperature, and the mixture was heated under reflux for 2 hours. After completion of the reaction, the reaction solution was cooled to room temperature, and aqueous ammonia (40 ml) was added. After stirring for 15 minutes, the reaction solution was filtered off with Celite, and the solvent was distilled off under reduced pressure. To the residue were added chloroform (100 ml) and anhydrous potassium carbonate, and the solution was shaken at 40° C. for 15 minutes. The reaction solution was filtered off with Celite, and the solvent was distilled off under reduced pressure. The residue was purified by vacuum distillation to give the title compound (3.96 g) as a pale yellow oily substance. Yield=80%.

b.p. 132–133° C. (7 mmHg)

¹H NMR(CDCl₃) δ 0.91(t, J=7 Hz, 3H), 1.26–1.36(m, 2H), 1.43–1.50(m, 2H), 1.60–1.67(m, 2H), 2.30–2.34(m, 2H), 2.40(t, J=8 Hz, 2H), 2.30–2.70(m, 8H), 2.74(t, J=7 Hz, 2H)

PREPARATION EXAMPLE 31

2-(4-Methyl-1-piperazinyl)ethylamine

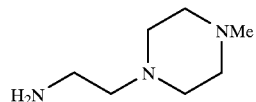

The title compound was synthesized by using N-[2-(4-methyl-1-piperazinyl)ethyl]phthalimide obtained in Preparation Example 3 according to the same process as in Preparation Example 30.

¹H NMR(CDCl₃) δ 2.28(s, 3H), 2.20–2.70(m, 8H), 2.42(t, J=6 Hz,2H), 2.78(t, J=6 Hz, 2H)

PREPARATION EXAMPLE 32

2-(4-n-Butyl-1-piperazinyl)ethylamine

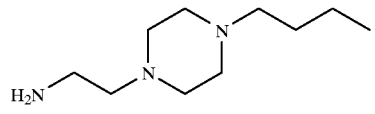

The title compound was synthesized by using N-[2-(4-n-butyl-1-piperazinyl)ethyl]phthalimide obtained in Preparation Example 21 according to the same process as in Preparation Example 30.

¹H NMR(CDCl₃) δ 0.91(t, J=7 Hz, 3H), 1.29–1.34(m, 2H), 1.43–1.51(m, 2H), 2.32(t, J=4 Hz, 2H), 2.30–2.60(m, 8H), 2.42(t, J=6 Hz, 2H), 2.77(t, J=6 Hz, 2H)

PREPARATION EXAMPLE 33

2-(4-p-Fluorobenzyl-1-piperazinyl)ethylamine

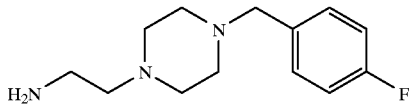

The title compound was synthesized by using N-[2-(4-p-fluorobenzyl-1-piperazinyl)ethyl]phthalimide obtained in Preparation Example 22 according to the same process as in Preparation Example 30.

¹H NMR(CDCl₃) δ 2.10–2.70(m, 8H), 2.42(t, J=6 Hz, 2H), 2.78(t,J=6 Hz, 2H), 3.47(s, 2H), 6.99(t, J=9 Hz, 2H), 7.27(dd, J=6 Hz, 9 Hz,2H)

PREPARATION EXAMPLE 34

2-(1-Methyl-4-piperidylidene)ethylamine

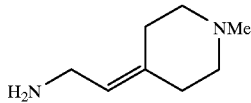

The title compound was synthesized by using N-[2-(1-methyl-4-piperidylidene)ethyl]phthalimide obtained in Preparation Example 23 according to the same process as in Preparation Example 30.

¹H NMR(CDCl₃) δ 2.22(t, J=6 Hz, 2H), 2.27(s, 3H), 2.29(t, J=6 Hz, 2H), 2.36–2.41(m, 4H), 3.27(d, J=7 Hz, 2H), 5.27(t, J=7 Hz, 1H)

PREPARATION EXAMPLE 35

2-(1-n-Butyl-4-piperidylidene)ethylamine

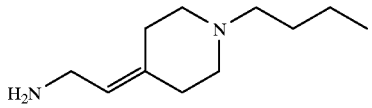

The title compound was synthesized by using N-[2-(1-n-butyl-4-piperidylidene)ethyl]phthalimide obtained in Preparation Example 24 according to the same process as in Preparation Example 30.

¹H NMR(CDCl₃) δ 0.91(t, J=7 Hz, 3H), 1.25–1.36(m, 2H), 1.44–1.52(m, 2H), 2.20–2.45(m, 10H), 3.27(d, J=7 Hz, 2H), 5.25(t, J=7 Hz, 1H)

PREPARATION EXAMPLE 36

2-(1-p-Fluorobenzyl-4-piperidylidene)ethylamine

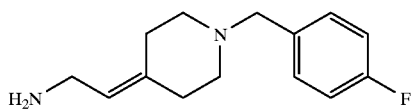

The title compound was synthesized by using N-[2-(1-p-fluorobenzyl-4-piperidylidene)ethyl]phthalimide obtained in Preparation Example 25 according to the same process as in Preparation Example 30.

¹H NMR(CDCl₃) δ 1.25(bs, 2H), 2.19(t, J=6 Hz, 2H), 2.26(t J=5 Hz, 2H), 2.38–2.43(m, 4H), 3.26(d, J=7 Hz, 2H), 3.46(s, 2H), 5.25(t, J=7 Hz, 1H), 6.97–7.01(m, 2H), 7.26–7.29(m, 2H)

PREPARATION EXAMPLE 37

(1-Methyl-4-piperidyl)methylamine

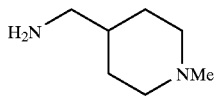

N-(1-Methyl-4-piperidyl)methylphthalimide (5.10 g) obtained in Preparation Example 26 was dissolved in ethanol (100 ml), hydrazine monohydrate (1.29 g) was added at room temperature, and the mixture was heated under reflux for 6 hours. After completion of the reaction, the reaction solution was cooled to room temperature, a 20% aqueous solution of sodium hydroxide (20 ml) was added. After stirring for 10 minutes, the reaction solution was distilled off under reduced pressure. To the residue were added chloroform (80 ml) and anhydrous potassium carbonate (30 g), and the mixture was stirred at 50° C. for 10 minutes. The reaction solution was filtered off with Celite, and the solvent was distilled off under reduced pressure. The residue was purified by vacuum distillation to give the title compound (1.56 g). Yield=61%.

b.p. 30–50° C. (4 mmHg)

¹H NMR(CDCl₃) δ 1.28–1.32(m, 2H), 1.42–1.56(m, 1H), 1.77(d, J=13 Hz, 2H), 2.03(dt, J=2 Hz,10 Hz, 2H), 2.29(s, 3H), 2.68(d, J=7 Hz, 2H), 2.91(d, J=12 Hz, 2H)

PREPARATION EXAMPLE 38

(1-n-Butyl-4-piperidyl)methylamine

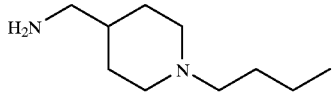

N-(1-n-Butyl-4-piperidyl)methylphthalimide (3.62 g) obtained in Preparation Example 27 was dissolved in methanol (100 ml), hydrazine monohydrate (0.87 g) was added at room temperature, and the mixture was stirred for 48 hours. The reaction solution was filtered off with Celite, aqueous ammonia (30 ml) was added, and the mixture was stirred for 10 minutes. Then, the volatiles were distilled off. To the residue were added chloroform and anhydrous potassium carbonate (25 g), and the mixture was shaken at 40° C. for 15 minutes. The reaction solution was filtered off with Celite, and the solvent was distilled away under reduced pressure to give the crude title compound (2.39 g) as an oily substance. This compound was used for the subsequent reaction without purification.

$^1$H NMR(CDCl$_3$) δ 0.91(t, J=7 Hz, 3H), 1.22–1.34(m, 5H), 1.48(sept, J=8 Hz, 5H), 1.71(d, J=9 Hz, 2H), 1.88(t, J=10 Hz, 2H), 2.30(t, J=8 Hz, 2H), 2.56(d, J=6 Hz, 2H), 2.95(d, J=12 Hz, 2H)

PREPARATION EXAMPLE 39

2-(1-Methyl-4-piperidyl)ethylamine

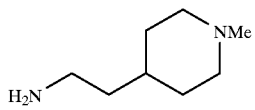

The title compound was synthesized by using N-[2-(1-methyl-4-piperidyl)ethyl]phthalimide obtained in Preparation Example 28 according to the same process as in Preparation Example 38.

$^1$H NMR(CDCl$_3$) δ 1.27–1.34(m, 2H), 1.42–1.49(m, 2H), 1.60–1.66(m, 1H), 1.72(t, J=13 Hz, 2H), 1.97–2.05(m, 2H), 2.24(d, J=6 Hz, 3H), 2.66(t, J=7 Hz, 1H), 2.85(t, J=11 Hz, 2H), 3.30–3.32(m,1H)

PREPARATION EXAMPLE 40

2-(1-n-Butyl-4-piperidyl)ethylamine

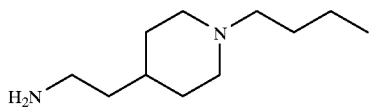

The title compound was synthesized by using N-[2-(1-n-butyl-4-piperidyl)ethyl]phthalimide obtained in Preparation Example 29 according to the same process as in Preparation Example 38.

$^1$H NMR(CDCl$_3$) δ 0.91(t, J=7 Hz, 3H), 1.22–1.40(m, 5H), 1.40–1.45(m, 2H), 1.45–1.62(m, 2H), 1.66(t, J=12 Hz, 2H), 1.87(t, J=11 Hz, 2H), 2.28(t, J=8 Hz, 2H), 2.72(t, J=7 Hz, 1H), 2.91(d, J=12 Hz, 2H), 3.43(t,J=7 Hz, 1H)

PREPARATION EXAMPLE 41

Diethyl 5-n-butyl-5-azanonanedioate

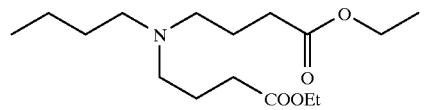

To ethyl 4-bromobutylate (25.7 g) was added n-butylamine (5.77 g), and the mixture was stirred at room temperature. A 10N aqueous solution of sodium hydroxide (30 ml) was added dropwise, and the mixture was stirred for 30 minutes. Then ammonium tetrabutyl hydrogensulfate (0.98 g) was added, and stirring further continued for one hour. The reaction solution was extracted with ether (200 ml), successively washed with water (100 ml) and saturated aqueous sodium chloride (100 ml), and dried over anhydrous magnesium sulfate. The solvent was distilled off under reduced-pressure. The residue was purified by silica gel column chromatography (ethyl acetate:hexane=1:10–1:0–chloroform:methanol=10:1) to give the title compound (10.2 g) as a colorless oily substance. Yield=51%.

$^1$H NMR(CDCl$_3$) δ 0.89(t, J=7 Hz, 3H), 1.25(t, J=7 Hz, 6H), 1.23–1.39(m, 4H), 1.69–1.76(m, 4H), 2.29–2.42(m, 10H), 4.12(q, J=7 Hz, 4H)

PREPARATION EXAMPLE 42

1-n-Butyl-5-octahydroazocinone

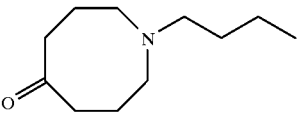

A suspension of potassium tert-butoxide (11.4 g) in toluene (1000 ml) was heated under reflux for 90 minutes, then a solution of diethyl 5-n-butyl-5-azanonanedioate (10.2 g) obtained in Preparation Example 41 in toluene (300 ml) was added dropwise over a period of one hour under reflux. The mixture was further heated under reflux for one hour. The solvent was distilled off at ordinary pressure, then to the residue was added water (400 ml). The mixture was shaken at 50° C. for 30 minutes to obtain a homogeneous solution, then hydrochloric acid (25 ml) was added thereto, and the mixture was heated under reflux for one hour. After the reaction solution was ice-cooled, the solution was made basic with anhydrous potassium carbonate, and extracted with chloroform (500 ml×3). The chloroform layer was dried over anhydrous magnesium sulfate, and the solvent was distilled off under reduced pressure. The residue was purified by silica gel column chromatography (methylene chloride:methanol:aqueous ammonia=90:10:0.5) to give the title compound (1.62 g) as a brown oily substance. Yield= 26%.

$^1$H NMR(CDCl$_3$) δ 0.88(t, J=7 Hz, 3H), 1.17–1.26(m, 2H), 1.32–1.40(m, 2H), 1.87–1.93(m, 4H), 2.19(t, J=6 Hz, 4H), 2.32(t, J=8 Hz, 2H), 2.49(t, J=6 Hz, 4H)

PREPARATION EXAMPLE 43

1-n-Butyl-5-octahydroazocinone oxime

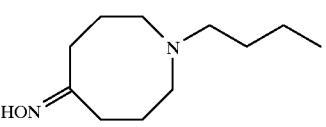

To a solution of 1-n-butyl-5-octahydroazocinone (1.62 g) obtained in Preparation Example 42 in methanol (20 ml) were successively added hydroxylamine hydrochloride (3.07 g) and 1,8-diazabicyclo[5.4.0]-7-undecane (1.61 g) at room temperature, and the mixture was stirred overnight. After the reaction solution was distilled off under reduced pressure, the residue was dissolved in water (40 ml), and the solution was made basic with potassium carbonate, extracted with chloroform (50 ml×3). The chloroform layer was dried over anhydrous magnesium sulfate, and the solvent was distilled off under reduced pressure. The residue was purified by silica gel column chromatography (methylene chloride:methanol:aqueous ammonia= 90:10:0.5) to give the title compound (1.60 g) as a pale yellow oily substance. Yield=91%.

$^1$H NMR(CDCl$_3$) δ 0.87(t, J=7 Hz, 3H), 1.22–1.38(m, 4H), 1.71–1.77(m, 4H), 2.23–2.26(m, 2H), 2.36–2.51(m, 8H), 7.60–7.68(m, 1H)

PREPARATION EXAMPLE 44

1-n-Butyl-5-octahydroazocinylamine

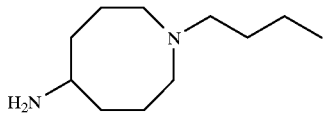

To a solution of 1-n-butyl-5-octahydroazocinone oxime (1.60 g) obtained Preparation Example 43 in n-pentyl alcohol (100 ml) was added metallic sodium (about 5 g) under reflux-heating, and the mixture was heated under reflux for 2 hours. After completion of the reaction, the mixture was allowed to cool to room temperature. Then water (150 ml) and hydrochloric acid were added, the reaction solution was made acidic, and washed with ethyl acetate (150 ml×2). The aqueous layer was made basic with sodium hydroxide, and extracted with chloroform (100 ml×3). The chloroform layer was dried over anhydrous magnesium sulfate, and the solvent was distilled off under reduced pressure to give the title compound (1.34 g) as a yellow oily substance. This compound was used for the subsequent reaction without purification.

$^1$H NMR(CDCl$_3$) δ 0.90(t, J=7 Hz, 3H), 1.26–1.33(m, 2H), 1.35–1.44(m, 2H), 1.51–1.62(m, 4H), 1.63–1.74(m, 4H), 2.40(t, J=7 Hz, 2H), 2.45(t, J=6 Hz, 4H), 3.26–3.36(m, 1H)

PREPARATION EXAMPLE 45

1-n-Propylindazole-3-carboxylic acid

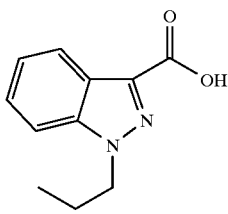

To a solution of 1H-indazole-3-carboxylic acid (5.00 g) in DMF (40 ml) was gradually added 60% sodium hydride (1.55 g) at 0° C. with stirring, and the mixture was stirred at room temperature for one hour. Then 1-bromopropane (4.55 g) was added, and the mixture was stirred overnight. The reaction solution was distilled off, dissolved in water, and washed with ethyl acetate. The aqueous layer was made acidic with hydrochloric acid, extracted with ethyl acetate, then the extract was dried over anhydrous magnesium sulfate, and decolorized with active carbon. After the solvent was distilled off, crystallization from ether gave the title compound (4.24 g) as crystals. Yield=67%.

$^1$H NMR(CDCl$_3$) δ 0.97(t, J=7 Hz, 3H), 2.03(sext, J=7 Hz, 2H), 4.47(t, J=7 Hz, 2H), 7.34–7.53(m, 3H), 8.27(d, J=8 Hz, 1H)

PREPARATION EXAMPLE 46

2-(4-Benzyl-1-piperazinyl)ethanol

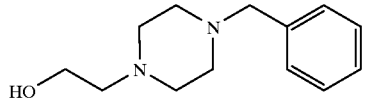

The title compound was synthesized by using 2-(1-piperazinyl)ethanol and benzyl bromide according to the same process as in Preparation Example 4.

$^1$H NMR(CDCl$_3$) δ 1.81(bs, 1H), 2.50(bs, 8H), 2.54(t, J=5 Hz, 2H), 3.51(s, 2H), 3.60(t, J=5 Hz, 2H), 7.23–7.27(m, 1H), 7.28–7.34(m, 4H )

PREPARATION EXAMPLE 47

N-[2-(4-Benzyl-1-piperazinyl)ethyl]phthalimide

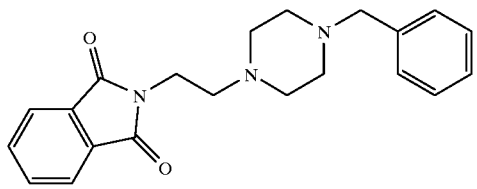

The title compound was synthesized by using 2-(4-benzyl-1-piperazinyl)ethanol obtained in Preparation Example 46 according to the same process as in Preparation Example 26.

$^1$H NMR(CDCl$_3$) δ 2.42(bs, 4H), 2.55(bs, 4H), 2.63(t, J=7 Hz, 2H), 3.47(s, 2H), 3.81(t, J=7 Hz, 2H), 7.21–7.30(m, 5H), 7.70–7.72(m, 2H), 7.83–7.85(m, 2H

PREPARATION EXAMPLE 48

2-(4-Benzyl-1-piperazinyl)ethylamine

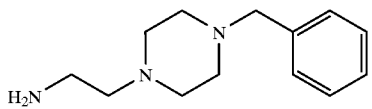

The title compound was synthesized by using N-[2-(4-benzyl-1-piperazinyl)ethyl]phthalimide obtained in Preparation Example 47 according to the same process as in Preparation Example 30.

$^1$H NMR(CDCl$_3$) δ 1.51(bs, 2H), 2.39–2.43(m, 6H), 2.47(bs, 4H), 2.77(t, J=6 Hz, 2H), 3.50(s, 2H), 7.22–7.27(m, 1H), 7.28–7.31(m,4H)

EXAMPLE 1

N-[3-(4-n-Butyl-1-piperazinyl)propyl]-1-n-propylindazole-3-carboxamide

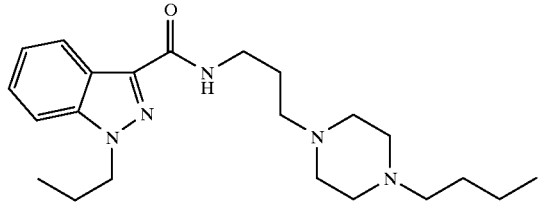

3-(4-n-Butyl-1-piperazinyl)propylamine (0.90 g) obtained in Preparation Example 30 was dissolved in DMF (20 ml), 1-n-propylindazole-3-carboxylic acid (0.92 g) obtained in Preparation Example 45 and diethylphosphorocyanidate (0.81 g) were successively added, and the mixture was stirred overnight. The reaction solution alas diluted with methylene chloride (200 ml), washed in turn with water (60 ml×3) and saturated aqueous sodium chloride (60 ml), dried over anhydrous magnesium sulfate, and the solvent was distilled off under reduced pressure. The residue was purified by silica gel column chromatography (methylene chloride:methanol=90:10) to give the title compound (1.01 g) as a pale yellow oily substance. Yield=58%.

$^1$H NMR(CDCl$_3$) δ 0.92(t, J=7 Hz, 3H), 0.94(t, J=7 Hz, 3H), 1.30–1.38(m, 2H), 1.46–1.53(m, 2H), 1.79–1.85(m, 2H), 1.93–2.02(m, 2H), 2.37(t, J=8 Hz, 2H), 2.30–2.80(m, 8H), 2.53(t, J=7 Hz, 2H), 3.59(dt, J=5 Hz, 6 Hz, 2H), 7.23–7.27(m, 1H), 7.37–7.42(m, 1H), 7.97(bs, 1H), 8.39(d, J=8 Hz, 1H)

Then the title compound was converted to the corresponding hydrochloride by a conventional method.

m.p. 188–194° C.

EXAMPLE 2

N-[2-(4-Methyl-1-piperazinyl)ethyl]-1-n-propylindazole-3-carboxamide

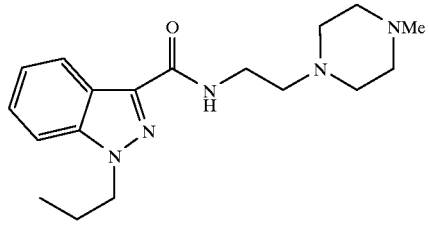

The title compound was synthesized by using 2-(4-methyl-1-piperazinyl)ethylamine obtained in Preparation Example 31 and 1-n-propylindazole-3-carboxylic acid obtained in Preparation Example 45 according to the same process as in Example 1.

$^1$H NMR(CDCl$_3$) δ 0.95(t, J=8 Hz, 3H), 1.96–2.01(m, 2H), 2.30(s, 3H), 2.30–2.70(m, 8H), 2.65(t, J=6 Hz, 2H), 3.61(dt, J=5 Hz, 6 Hz, 2H), 4.35(t, J=7 Hz, 2H), 7.24–7.28 (m, 1H), 7.38–7.41(m, 3H), 8.37(d, J=8 Hz, 1H)

Then the title compound was converted to the corresponding hydrochloride by a conventional method.

m.p. 186–193° C.

EXAMPLE 3

N-[2-(4-n-Butyl-1-piperazinyl)ethyl]-1-n-propylindazole-3-carboxamide

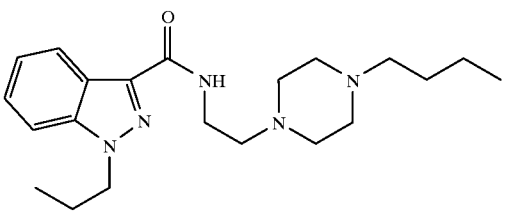

The title compound was synthesized by using 2-(4-n-butyl-1-piperazinyl)ethylamine obtained in Preparation Example 32 and 1-n-propylindazole-3-carboxylic acid obtained in Preparation Example 45 according to the same process as in Example 1.

$^1$H NMR(CDCl$_3$) δ 0.91(t, J=7 Hz, 3H), 0.94(t, J=7 Hz, 3H), 1.28–1.34(m, 2H), 1.43–1.49(m, 2H), 1.97–2.03(m, 2H), 2.34(t, J=8 Hz, 2H), 2.40–2.80(m, 8H), 2.86(t, J=6 Hz, 2H), 4.44(t, J=7 Hz, 2H), 4.57(t, J=6 Hz, 2H), 7.29–7.33(m, 1H), 7.42–7.49(m, 2H), 8.24(d, J=8 Hz, 1H)

Then the title compound was converted to the corresponding hydrochloride by a conventional method.

m.p. 204–207° C.

EXAMPLE 4

N-[2-(1-Methyl-4-piperidylidene)ethyl]-1-n-propylindazole-3-carboxamide

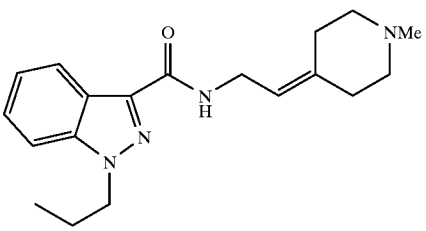

The title compound was synthesized by using 2-(1-methyl-4-piperidylidene)ethylamine obtained in Preparation Example 34 and 1-n-propylindazole-3-carboxylic acid obtained in Preparation Example 45 according to the same process as in Example 1.

$^1$H NMR(CDCl$_3$) δ 0.94(t, J=7 Hz, 3H), 1.94–2.02(m, 2H), 2.30(t,J=6 Hz, 2H), 2.31(s, 3H), 2.43–2.48(m, 6H), 4.11(d, J=5 Hz, 6 Hz, 2H), 4.34(t, J=7 Hz, 2H), 5.38(t, J=7 Hz, 1H), 6.91–7.00(m, 1H), 7.24–7.28(m, 1H), 7.40–7.41 (m, 2H), 8.38(d, J=8 Hz, 1H)

Then the title compound was converted to the corresponding hydrochloride by a conventional method.

IR(KBr) 3420, 2962, 2936, 1652, 1538, 1198, 754cm$^{-1}$

EXAMPLE 5

N-[2-(1-n-Butyl-4-piperidylidene)ethyl]-1-n-propylindazole-3-carboxamide

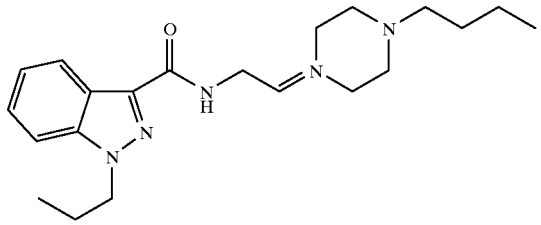

The title compound was synthesized by using 2-(1-n-butyl-4-piperidylidene)ethylamine obtained in Preparation Example 35 and 1-n-propylindazole-3-carboxylic acid obtained in Preparation Example 45 according to the same process as in Example 1.

$^1$H NMR(CDCl$_3$) δ 0.92(t, J=7 Hz, 3H), 0.94(t, J=8 Hz, 3H), 1.28–1.38(m, 2H), 1.51–1.59(m, 2H), 1.92–2.02(m, 2H), 2.25–2.39(m, 2H), 2.39–2.52(m, 4H), 2.52–2.70(m, 4H), 4.10(t, J=6 Hz, 2H), 4.34(t, J=7 Hz, 2H), 5.38(t, J=7 Hz, 1H), 6.89–7.01(m, 1H), 7.24–7.28(m, 1H), 7.40–7.41 (m, 2H), 8.38(d, J=8 Hz, 1H)

Then the title compound was converted to the corresponding hydrochloride by a conventional method.

m.p. 162–167° C.

EXAMPLE 6

N-(1-n-Butyl-5-octahydroazocinyl)-1-n-propylindazole-3-carboxamide

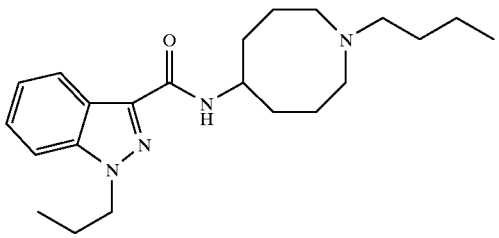

The title compound was synthesized by using 1-n-butyl-5-octahydroazocinylamine obtained in Preparation Example 44 and 1-n-propylindazole-3-carboxylic acid obtained in Preparation Example 45 according to the same process as in Example 1.

$^1$H NMR(CDCl$_3$) δ 0.91–0.96(m, 6H), 1.28–1.40(m, 4H), 1.59–1.83(m, 8H), 1.91–2.00(m, 2H), 2.40–2.70(m, 4H), 4.22–4.29(m,2H), 4.32(t, J=7 Hz, 2H), 4.68–4.83(m, 1H), 7.22–7.26(m, 1H), 7.35–7.41(m, 2H), 8.41(d, J=8 Hz, 1H), 8.52–8.66(m, 1H)

Then the title compound was converted to the corresponding hydrochloride by a conventional method.

IR(KBr) 2938, 2876, 2822, 1652, 1533, 1492, 1196, 1035, 754 cm$^{-1}$

EXAMPLE 7

N-(1-Methyl-4-piperidyl)methyl-1-n-propylindazole-3-carboxamide

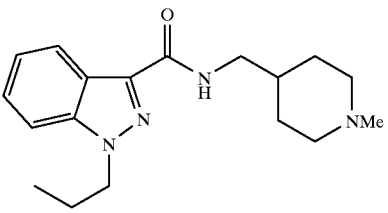

The title compound was synthesized by using (1-methyl-4-piperidyl)methylamine obtained in Preparation Example 37 and 1-n-propylindazole-3-carboxylic acid obtained in Preparation Example 45 according to the same process as in Example 1.

$^1$H NMP(CDCl$_3$) δ 0.95(t, J=7 Hz, 3H), 1.42–1.47(m, 2H), 1.62–1.75(m, 1H), 1.95–2.10(m, 4H), 1.97(sext, J=7 Hz, 2H), 1.95–2.10(m, 3H), 2.30(s, 3H), 2.91(d, J=12 Hz, 2H), 3.40(t, J=5 Hz, 2H), 4.34(t, J=6 Hz, 2H), 7.10–7.15(m, 1H), 7.24–7.28(m, 1H), 7.40–7.41(m, 2H), 8.38(d, J=8 Hz, 1H)

Then the title compound was converted to the corresponding hydrochloride by a conventional method.

m.p. 115–135° C.

EXAMPLE 8

N-[2-(1-Methyl-4-piperidyl)ethyl]-1-n-propylindazole-3-carboxamide

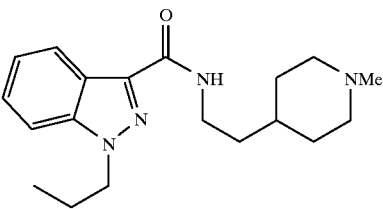

The title compound was synthesized by using 2-(1-methyl-4-piperidyl)ethylamine obtained in Preparation Example 39 and 1-n-propylindazole-3-carboxylic acid obtained in Preparation Example 45 according to the same process as in Example 1.

$^1$H NMR(CDCl$_3$) δ 0.94(t, J=7 Hz, 3H), 1.25–1.37(m, 3H), 1.62(dd, J=6 Hz, 15 Hz, 2H), 1.77(dd, J=1 Hz, 12 Hz, 2H), 1.89–1.98(m, 4H), 2.26(s, 3H), 2.84(d, J=12 Hz, 2H), 3.53(q, J=5 Hz, 2H), 4.34(t, J=7 Hz, 2H), 7.25(bs, 1H), 7.25–7.28(m, 1H), 7.40–7.41(m, 2H), 8.38(d, J=8 Hz, 1H)

Then the title compound was converted to the corresponding hydrochloride by a conventional method.

EXAMPLE 9

N-[2-(1-p-Fluorobenzyl-4-piperidylidene)ethyl]-1H-indazole-3-carboxamide

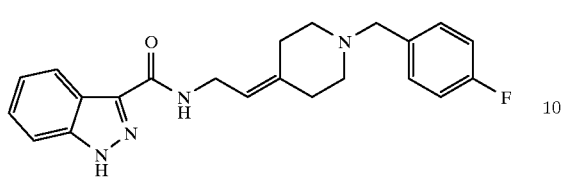

2-(1-p-Fluorobenzyl-4-piperidylidene)ethylamine (0.60 g) obtained in Preparation Example 36 was dissolved in DMF (10 ml), diindazolo[2,3-a] [2',3'-d]pyrazine-7,14-dione (0.44 g), N,N-dimethylaminopyridine (0.05 g) and anhydrous potassium carbonate (0.53 g) were successively added, and the mixture was stirred overnight. The reaction solution was diluted with ethyl acetate (150 ml), washed with water (50 ml×3), dried over anhydrous magnesium sulfate, and distilled off under reduced pressure. The residue was purified by silica gel column chromatography (methylene chloride:methanol=90:10) to give the title compound (0.73 g) as a pale yellow oily substance. Yield=75%.

$^1$H NMR(CDCl$_3$) δ 2.24(t, J=5 Hz, 2H), 2.37(t, J=5 Hz, 2H), 2.44(t, J=5 Hz, 4H), 3.48(s, 2H), 4.10(dd, J=5 Hz, 6 Hz, 2H), 5.33(t, J=7 Hz, 1H), 6.96–7.02(m, 3H), 7.25–7.30(m, 3H), 7.41(dt, J=1 Hz, 8 Hz, 1H), 7.47(d, J=8 Hz, 1H), 8.41(d, J=8 Hz, 1H), 10.82(bs 1H)

Then the title compound was converted to the corresponding hydrochloride by a conventional method.

m.p. 147–152° C.

EXAMPLE 10

N-[2-(4-n-Butyl-1-piperazinyl)ethyl]-1H-indazole-3-carboxamide

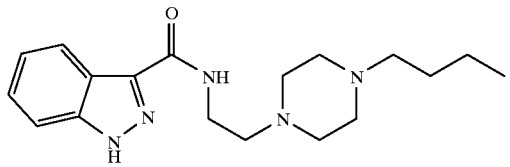

The title compound was synthesized by using 2-(4-n-butyl-1-piperazinyl)ethylamine obtained in Preparation Example 32 and diindazolo[2,3-a][2',3'-d]pyrazine-7,14-dione according to the same process as in Example 9.

$^1$H NMR(CDCl$_3$) δ 0.91(t, J=7 Hz, 3H), 1.25–1.36(m, 2H), 1.44–1.52(m, 2H), 2.35(t, J=8 Hz, 2H), 2.30–2.80(m, 8H), 2.68(t, J=6 Hz, 2H), 3.64(dt, J=5 Hz, 6 Hz, 2H), 7.26(t, J=8 Hz, 1H), 7.41(t, J=8 Hz, 1H), 7.49(t, J=8 Hz, 1H), 7.63(bs, 1H), 8.36(d, J=8 Hz, 1H), 10.95(bs, 1H)

EXAMPLE 11

N-[2-(4-p-Fluorobenzyl-1-piperazinyl)ethyl]-1H-indazole-3-carboxamide

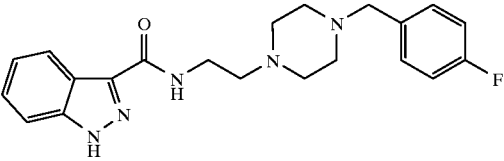

The title compound was synthesized by using 2-(4-p-fluorobenzyl-1-piperazinyl)ethylamine obtained in Preparation Example 33 and diindazolo[2,3-a][2',3'-d]pyrazine-7, 14-dione according to the same process as in Example 9.

$^1$H NMR(CDCl$_3$) δ 2.51(bs, 4H), 2.63(bs, 4H), 2.71(t, J=6 Hz, 2H), 3.46(s, 2H), 3.67(dt, J=5 Hz, 6 Hz, 2H), 6.98(t, J=8 Hz, 2H), 7.00–7.26(m, 3H), 7.33–7.37(m, 1H), 7.42(d, J=9 Hz, 1H), 7.81(t,J=5 Hz, 1H), 8.29(d, J=8 Hz, 1H), 11.88(bs, 1H)

Then the title compound was converted to the corresponding hydrochloride by a conventional method.

m.p. 228–238° C. (dec.)

EXAMPLE 12

N-[2-(1-p-Fluorobenzyl-4-piperidylidene)ethyl]-1-n-propylindazole-3-carboxamide

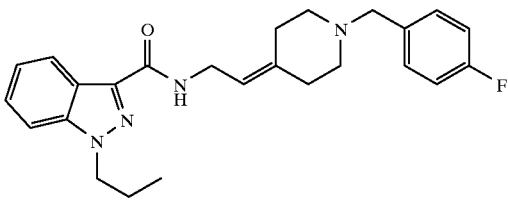

N-[2-(1-p-Fluorobenzyl-4-piperidylidene)ethyl]-1H-indazole-3-carboxamide (0.33 g) obtained In Example 9 was dissolved in DMF (5 ml), 60% sodium hydride (0.05 g) and 1-bromopropane (0.21 g) were successively added under ice-cooling, and the mixture was stirred overnight at room temperature. The reaction solution was diluted with ethyl acetate (50 ml), washed with water (20 ml×4), dried over anhydrous magnesium sulfate, and distilled off under reduced pressure. The residue was purified by silica gel column chromatography (ethyl acetate:hexane=1:1) to give the title compound (0.15 g). Yield=41%.

$^1$H NMR(CDCl$_3$) δ 0.94(t, J=7 Hz, 3H), 1.92–2.02(m, 2H), 2.24(t,J=5 Hz, 2H), 2.38(t, J=5 Hz, 2H), 2.44(bs, 4H), 3.47(s, 2H), 4.08–4.12(m, 2H), 4.33(dd, J=7 Hz, 7 Hz, 2H), 5.35(t, J=7 Hz, 1H), 6.90(bs, 1H), 6.99(t, J=9 Hz, 1H), 7.23–7.30(m, 3H), 7.39–7.40(m, 2H), 8.38(d, J=8 Hz, 1H)

Then the title compound was converted to the corresponding hydrochloride by a conventional method.

m.p. 192–201° C. (dec.) $^1$H NMR(D$_2$O) δ 0.84(t, J=8 Hz, 3H), 1.89–1.96(m, 2H), 2.30–2.60(m, 1H), 2.54(bs, 2H), 2.80–3.20(m, 3H), 3.40–3.80(m, 2H), 4.09(bs, 2H), 4.33(s, 2H), 4.40(t, J=7 Hz, 2H), 5.61(t, J=7 Hz, 2H), 7.26(t, J=9 Hz, 2H), 7.37(t, J=8 Hz, 1H), 7.51–7.55(m, 3H), 7.65(d, J=8 Hz, 1H), 8.09(d, J=8 Hz, 1H)

EXAMPLE 13

N-[2-(4-n-Butyl-1-piperazinyl)ethyl]-1-sec-butylindazole-3-carboxamide

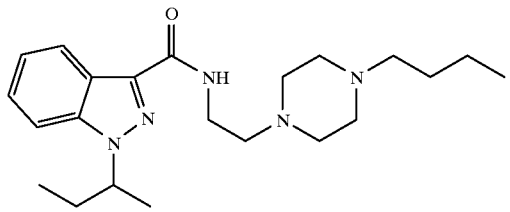

The title compound was synthesized by using N-[2-(4-n-butyl-1-piperazinyl)ethyl]-1H-indazole-3-carboxamide obtained in Example 10 and 2-bromobutane according to the same process as in Example 12.

$^1$H NMR(CDCl$_3$) δ 0.80(t, J=7 Hz, 3H), 0.92(t, J=7 Hz, 3H), 1.30–1.37(m, 2H), 1.45–1.53(m, 2H), 1.59(d, J=7 Hz, 2H), 1.86–1.97(m, 1H), 2.05–2.17(m, 1H), 2.36(t, J=8 Hz, 2H), 2.30–2.80(m, 8H), 2.66(t, J=6 Hz, 2H), 3.55–3.65(m, 2H), 4.57–4.62(m, 1H), 7.24–7.27(m, 1H), 7.36–7.47(m, 3H), 8.37(d, J=8 Hz, 1H)

Then the title compound was converted to the corresponding hydrochloride by a conventional method.

m.p. 168–172° C. (dec.)

$^1$H NMPR(D$_2$O) δ 0.75(t, J=7 Hz, 3H), 0.99(t, J=7 Hz, 3H), 1.41–1.50(m, 2H), 1.62(d, J=6 Hz, 2H), 1.76–1.83(m, 2H), 1.96–2.12(m,2H), 3.34(t, J=8 Hz, 2H), 3.50–4.10(m, 8H), 3.61(t, J=6 Hz, 2H), 3.96(t, J=6 Hz, 2H), 4.83–4.87(m, 1H), 7.44(t, J=8 Hz, 1H), 7.59(t, J=8 Hz, 1H), 7.80(t, J=8 Hz, 1H), 8.18(t, J=8 Hz, 1H)

EXAMPLE 14

N-[2-(4-n-Butyl-1-piperazinyl)ethyl]-1-(3-pentyl)indazole-3-carboxamide

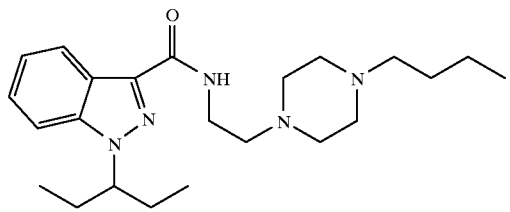

The title compound was synthesized by using N-[2-(4-n-butyl-1-piperazinyl)ethyl]-1H-indazole-3-carboxamide obtained in Example 10 and 3-pentyl bromide according to the same process as in Example 12.

$^1$H NMR(CDCl$_3$) δ 0.74(t, J=7 Hz, 6H), 0.92(t, J=7 Hz, 3H), 1.28–1.37(m, 2H), 1.45–1.53(m, 2H), 1.88–1.99(m, 2H), 2.04–2.16(m, 2H), 2.35(t, J=8 Hz, 2H), 2.40–2.70(m, 8H), 2.66(t, J=7 Hz, 2H), 3.55–3.65(m, 2H), 7.23–7.27(m, 1H), 7.36–7.47(m, 3H), 8.38(d, J=8 Hz, 1H)

Then the title compound was converted to the corresponding hydrochloride by a conventional method.

m.p. 146–149° C.

$^1$H NMR(D$_2$O) δ 0.71(t, J=8 Hz, 6H), 0.99(t, J=7 Hz, 3H), 1.42–1.48(m, 2H), 1.75–1.81(m, 2H), 2.02–2.11(m, 4H), 3.34(t, J=8 Hz, 2H), 3.50–4.00(m, 8H), 3.58(t, J=6 Hz, 2H), 3.95(t, J=6 Hz, 2H), 7.45(t, J=8 Hz, 1H), 7.61(t, J=8 Hz, 1H), 7.84(d, J=9 Hz, 1H), 8.20(d, J=8 Hz, 1H)

EXAMPLE 15

N-[2-(4-p-Fluorobenzyl-1-piperazinyl)ethyl]-1-n-propylindazole-3-carboxamide

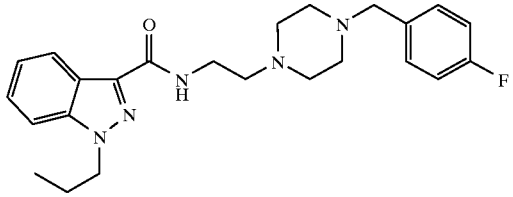

The title compound was synthesized by using N-[2-(4-p-fluorobenzyl-1-piperazinyl)ethyl]-1H-indazole-3-carboxamide obtained in Example 11 and 1-bromopropane according to the same process as in Example 12.

$^1$H NMR(CDCl$_3$) δ 0.95(t, J=7 Hz, 3H), 1.94–2.03(m, 2H), 2.30–2.70(m, 8H), 2.64(t, J=6 Hz, 2H), 3.48(s, 2H), 3.53–3.66(m, 2H), 4.35(t, J=7 Hz, 2H), 6.97–7.01(m, 2H), 7.24–7.30(m, 3H), 7.35–7.43(m, 3H), 8.37(d, J=8 Hz, 1H)

Then the title compound was converted to the corresponding hydrochloride by a conventional method.

m.p. 178–188° C.

$^1$H NMR(D$_2$O) δ 0.86(t, J=7 Hz, 3H), 1.95–2.00(m, 2H), 3.56(t, J=6 Hz, 2H), 3.60–3.80(bm, 8H), 3.92(t, J=6 Hz, 2H), 4.48–4.51(m, 2H), 7.30(t, J=9 Hz, 2H), 7.43(t, J=8 Hz, 1H), 7.56–7.61(m, 3H), 7.75(d, J=9 Hz, 1H), 8.15(d, J=8 Hz, 1H)

EXAMPLE 16

N-[2-(4-p-Fluorobenzyl-1-piperazinyl)ethyl]-1-allylindazole-3-carboxamide

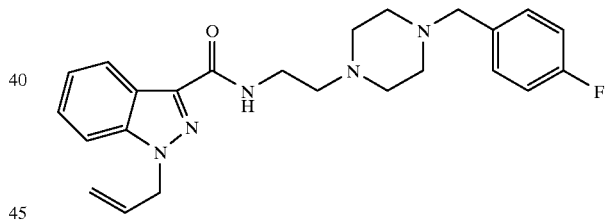

The title compound was synthesized by using N-[2-(4-p-fluorobenzyl-1-piperazinyl)ethyl]-1H-indazole-3-carboxamide carboxamide obtained in Example 11 and allyl bromide according to the same process as in Example 12.

$^1$H NMR(CDCl$_3$) δ 2.30–2.70(m, 4H), 2.63(t, J=7 Hz, 2H), 3.48(s, 2H), 3.52–3.65(m, 2H), 5.03(d, J=5 Hz, 2H), 5.16(d, J=17 Hz, 1H), 5.26(d, J=10 Hz, 1H), 6.04(ddd, J=5 Hz, 10 Hz, 17 Hz, 1H), 6.97–7.02(m, 2H), 7.24–7.30(m, 3H), 7.36(bt, J=5 Hz, 1H), 7.40(d, J=4 Hz, 1H), 8.38(d, J=8 Hz, 1H)

Then the title compound was converted to the corresponding hydrochloride by a conventional method.

m.p. 193–196° C.

$^1$H NMR(D$_2$O) δ 3.42(t, J=6 Hz, 2H), 3.55(bs, 8H), 3.87(t, J=6 Hz,2H), 4.39(s, 2H), 5.06(d, J=18 Hz, 1H), 5.15(d, J=5 Hz, 2H), 5.29(d, J=10 Hz, 1HH), 6.12(ddd, J=5 Hz, 10 Hz, 18 Hz, 1H), 7.28(t, J=9 Hz, 2H), 7.42(t, J=8 Hz, 1H), 7.53–7.60(m, 3H), 7.69(d, J=9 Hz), 8.14(d, J=8 Hz, 1H)

EXAMPLE 17

N-(1-Benzyl-4-piperidyl)-1-n-propylindazole-3-carboxamide

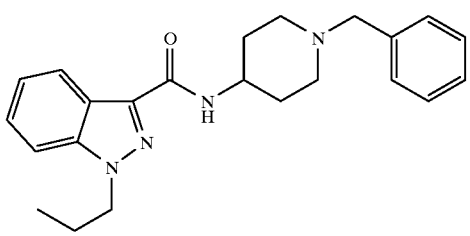

To a solution of 1-n-propylindazole-3-carboxylic acid (0.50 g) obtained in Preparation Example 45 and 1-benzyl-4-piperidylamine (0.51 g) in DMF (20 ml) were added 1-ethyl-3-(3-dimethylaminopropyl)carbodiimide hydrochloride (0.52 g) and 1-hydroxybenzotriazole monohydrate (0.36 g) under ice-cooling, and the mixture was stirred at room temperature for 12 hours. To the reaction solution were added water and ethyl acetate, extracted with ethyl acetate, dried over anhydrous potassium carbonate, and the solvent was distilled off under reduced pressure. The residue was purified by silica gel column chromatography (ethyl acetate:hexane=4:1) to give the title compound (0.70 g) as a yellow oily substance. Yield=78%.

$^1$H NMR(CDCl$_3$) δ 0.93(t, J=7 Hz, 3H), 1.58–1.72(m, 2H), 1.96(sext, J=7 Hz, 2H), 2.04(d, J=10 Hz, 2H), 2.19(t, J=11 Hz, 2H), 2.86–2.92(m, 2H), 3.52(s, 2H), 4.05–4.32(m, 1H), 4.33(t, J=7 Hz,2H), 6.93(d, J=8 Hz, 1H), 7.22–7.41(m, 8H), 8.37(t, J=8 Hz, 1H)

Then the title compound was converted to the corresponding hydrochloride by a conventional method.

m.p. 191–194° C.

EXAMPLE 18

N-(1-n-Butyl-4-piperidyl)methyl-1-n-propylindazole-3-carboxamide

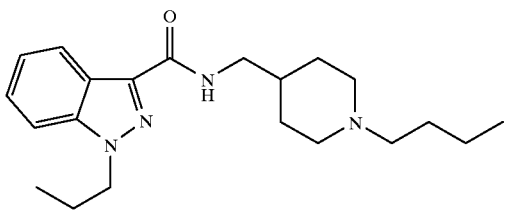

The title compound was synthesized by using (1-n-butyl-4-piperidyl)methylamine obtained in Preparation Example 38 and 1-n-propylindazole-3-carboxylic acid obtained in Preparation Example 45 according to the same process as in Example 17.

$^1$H NMR(CDCl$_3$) δ 0.91(t. J=8 Hz, 3H), 0.95(t, J=7 Hz, 3H), 1.30(sext, J=7 Hz, 2 Hz), 1.43–1.46(m, 2H), 1.48(sept, J=7 Hz, 2H), 1.62–1.76(m, 1H), 1.80(d, J=13 Hz, 2H), 1.93(t, J=11 Hz, 2H), 1.97(sext, J=7 Hz, 2H), 2.32(t, J=8 Hz, 2H), 2.97(d, J=11 Hz, 2H), 3.40(t, J=6 Hz, 2H), 4.34(t, J=7 Hz, 2H), 7.10–7.13(m, 1H), 7.37–7.42(m, 2H), 8.38(d, J=8 Hz, 1H)

Then the title compound was converted to the corresponding hydrochloride by a conventional method.

m.p. 151–152° C.

EXAMPLE 19

N-[2-(1-n-Butyl-4-piperidyl)ethyl]-1-n-propylindazole-3-carboxamide

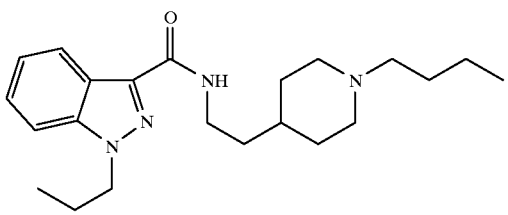

The title compound was synthesized by using 2-(1-n-butyl-4-piperidyl)ethylamine obtained in Preparation Example 40 and 1-n-propylindazole-3-carboxylic acid obtained in Preparation Example 45 according to the same process as in Example 17.

$^1$H NMR(CDCl$_3$) δ 0.93(t, J=7 Hz, 3H), 0.95(t, J=7 Hz, 3H), 1.34(sext, J=7 Hz, 3H), 1.49–1.61(m, 1H), 1.63–1.80 (m, 4H), 1.91(d,J=15 Hz, 2H), 1.97(sext, J=7 Hz, 2H), 2.25–2.40(m, 2H), 2.56–2.66(m, 2H), 3.18–3.29(m, 2H), 3.54(q, J=7 Hz, 2H), 4.35(t, J=7 Hz, 2H), 7.01(t, J=6 Hz, 1H), 7.25–7.29(m, 1H), 7.39–7.42(m, 2H), 8.36(d, J=8 Hz, 1H)

Then the title compound was converted to the corresponding hydrochloride by a conventional method.

m.p. 150–151° C.

EXAMPLE 20

N-(4-Piperidyl)-1-n-propylindazole-3-carboxamide

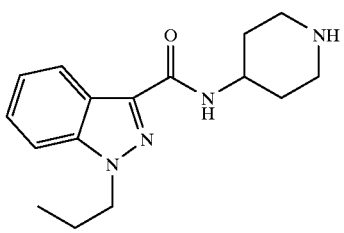

To a solution of N-(1-benzyl-4-piperidyl)-1-n-propylindazole-3-carboxamide hydrochloride (0.70 g) obtained in Example 17 in methanol (40 ml) was added a suspension of 10% palladium carbon (2.80 g) in methanol, and the mixture was stirred at room temperature under hydrogen atmosphere at ordinary pressure for one hour. The reaction solution was filtered off with Celite, and distilled off under reduced pressure to give the hydrochloride (0.50 g) of the title compound. Yield=94%.

$^1$H NMR(CDCl$_3$) δ 0.96(t, J=7 Hz, 3H), 1.99(q, J=7 Hz, 2H), 2.08–2.20(m, 2H), 2.20–2.36(m, 2H), 3.09(bs, 2H), 3.50–3.64(m, 2H), 4.20–4.37(m, 1H), 4.37(t, J=7 Hz, 2H), 7.27–7.29(m, 1H), 7.40–7.46(m, 2H), 8.31(d, J=8 Hz, 1H)

m.p. 188–210° C.

EXAMPLE 21

N-(4-Piperidyl)methyl-1-n-propylindazole-3-carboxamide

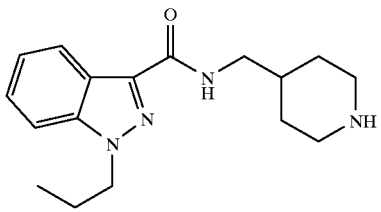

A solution of N-(1-methyl-4-piperidyl)methyl-1-n-propylindazole-3-carboxamide (2.00 g) obtained in Example 7 in α-chloroethyl chloroformate (8 ml) was stirred at 70° C. for 6 hours, then methanol (20 ml) was added, and the mixture was heated under reflux for 2 hours. The reaction solution was distilled off under reduced pressure. The residue was purified by silica gel column chromatography (chloroform:methanol:aqueous ammonia=90:10:1) to give the title compound (0.40g) as a yellow oily substance. Yield=21%.

$^1$H NMR(CDCl$_3$) δ 0.95(t, J=7 Hz, 3H), 1.31–1.35(m, 2H), 1.84(d,J=12 Hz, 2H), 1.98(sext, J=7 Hz, 2H), 2.42(bs, 1H), 2.66(td, J=2 Hz,12 Hz, 2H), 3.18(d, J=12 Hz, 2H), 3.39(t, J=6 Hz, 2H), 4.34(t, J=7 Hz, 2H), 7.10–7.25(m, 1H), 7.25–7.29(m, 1H), 7.40–7.41(m, 2H), 8.37(dd, J=1 Hz, 8 Hz, 1H)

Then the title compound was converted to the corresponding hydrochloride by a conventional method.

EXAMPLE 22

N-(1-Methyl-4-piperidyl)-1-n-propylindazole-3-carboxamide

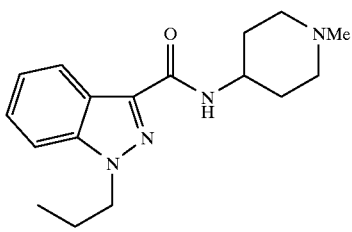

To N-(4-piperidyl)-1-n-propylindazole-3-carboxamide hydrochloride (0.32 g) obtained in Example 20 were added formic acid (0.7 ml) and a 36% aqueous solution of formaldehyde (0.3 ml), and the mixture was stirred at room temperature for 5 hours. Then formic acid (4 ml) and a 36% aqueous solution of formaldehyde (1.6 ml) were further added, and the mixture was heated under reflux for 2.5 hours. The reaction solution was distilled off under reduced pressure, and to the residue were added chloroform and aqueous ammonia. After extraction with chloroform, the chloroform layer was washed with saturated aqueous sodium chloride, dried over anhydrous potassium carbonate, and distilled off under reduced pressure. The residue was purified by silica gel column chromatography (chloroform methanol:aqueous ammonia 90:10:2) to give the title compound (0.06 g). Yield 18%.

$^1$H NMR(CDCl$_3$) δ 0.95(t, J=7 Hz, 3H), 1.63–1.69(m, 2H), 1.98(sext, J=7 Hz, 2H), 2.08(dd, J=2 Hz, 10 Hz, 2H), 2.20(t, J=11 Hz, 2H), 2.33(s, 3H), 2.87(d, J=12 Hz, 2H), 4.00–4.10(m, 1H), 4.35(t,J=7 Hz, 2H), 6.88(d, J=8 Hz, 1H), 7.24–7.28(m, 1H), 7.37–7.42(m,2H), 8.37(d, J=8 Hz, 1H)

Then the title compound was converted to the corresponding hydrochloride by a conventional method.

EXAMPLE 23

N-(1-n-Butyl-4-piperidyl)-1-n-propylindazole-3-carboxamide

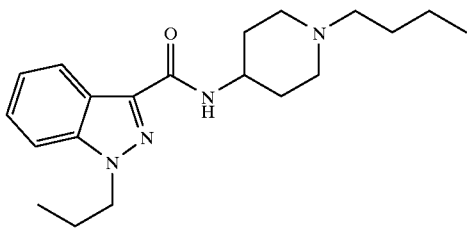

To a suspension of N-(4-piperidyl)-1-n-propylindazole-3-carboxamide hydrochloride (0.52 g) obtained in Example 20 in acetonitrile were successively added 50% potassium fluoride—Celite (1.10 g) and 1-bromobutane (0.22 ml), and the mixture was heated under reflux for 11 hours. The reaction solution was filtered off, distilled off under reduced pressure, and to the residue was added chloroform and saturated aqueous sodium hydrogencarbonate. After extraction with chloroform, the chloroform layer was dried over anhydrous potassium carbonate, and distilled off under reduced pressure. The residue was purified by silica gel column chromatography (chloroform:methanol=20:1) to give the title compound (0.42 g) as a yellow oily substance. Yield=69%.

$^1$H NMR(CDCl$_3$) δ 0.93(t, J=8 Hz, 3H), 0.95(t, J=8 Hz, 3H), 1.33(sext, J=8 Hz, 2H), 1.46–1.54(m, 2H), 1.61–1.70 (d, 2H), 1.98(sext, J=7 Hz, 2H), 2.07(bd, J=12 Hz, 2H), 2.16(bt, H=11 Hz, 2H), 2.37(t, J=8 Hz, 2H), 2.94(bd, J=12 Hz, 2H), 4.04–4.07(m, 1H), 4.35(t, J=7 Hz, 2H), 6.90(d, J=8 Hz, 1H), 7.24–7.28(m, 1H), 7.37–7.43(m, 2H), 8.37(d, J=8 Hz, 1H)

Then the title compound was converted to the corresponding hydrochloride by a conventional method.

EXAMPLE 24

N-[2-(4-Benzyl-1-piperazinyl)ethyl]-1-n-propylindazole-3-carboxamide

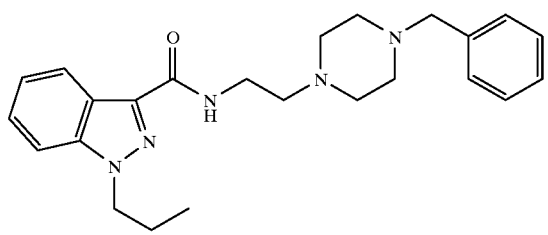

To a solution of 2-(4-benzyl-1-piperazinyl)-ethylamine (2.19 g) obtained in Preparation Example 48 in DMF (150 ml) were successively added at room temperature 1-n-propylindazole-3-carboxylic acid (2.04 g), triethylamine (1.52 g) and diethyl phosphorocyanidate (1.95 g) with stirring, and the mixture was stirred at room temperature for 12 hours. The reaction solution was distilled off, and the residue obtained was purified by silica gel column chromatography (ethyl acetate-chloroform:methanol aqueous ammonia=10:1:0.05) to give the title compound (3.76 g) as a brown oily substance. Yield 90%.

$^1$H NMR(CDCl$_3$) δ 0.96(t, J=7 Hz, 3H), 1.94–2.02(m, 2H), 2.54(bs, 4H), 2.59(bs, 4H), 2.66(t, J=6 Hz, 2H), 3.54(s, 2H), 3.59–3.64(m, 2H), 4.36(t, J=7 Hz, 2H), 7.24–7.43(m, 9H), 8.37(d, J=8 Hz, 1H)

EXAMPLE 25

N-[2-(4-Allyl-1-piperazinyl)ethyl]-1-n-propylindazole-3-carboxamide

EXAMPLE 25-1

Synthesis of N-[2-(4H-1-piperazinyl)ethyl]-1-n-propylindazole-3-carboxamide dihydrochloride

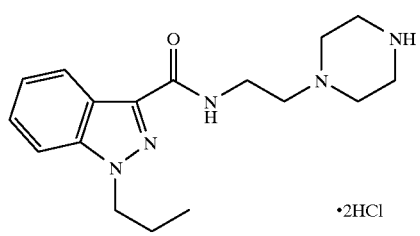

·2HCl

To a solution of N-[2-(4-benzyl-1-piperazinyl)-ethyl]-1-n-propylindazole-3-carboxamide (0.96 g) obtained in Example 24 in methanol (50 ml) in 100 ml Margen type apparatus for a catalytic reduction were successively added 4N hydrochloric acid-ethyl acetate solution (2 ml) and 10% palladium-carbon powder (0.31 g), and the mixture was shaken at room temperature under hydrogen atmosphere for 30 minutes. The insolubles were filtered off with Celite, and the filtrate was concentrated under reduced pressure to give the title compound (1.10 g) as a white, amorphous substance. This compound was used for the subsequent reaction without purification.

$^1$H NMR(CDCl$_3$) δ 0.86(t, J=7 Hz, 3H), 1.92–2.01(m, 2H), 3.67(t, J=6 Hz, 2H), 3.73(bs, 4H), 3.86(bs, 4H), 3.94–4.01(m, 2H), 4.47(t, J=7 Hz, 2H), 7.40(t, J=8 Hz, 1H), 7.56(t, J=8 Hz, 1H), 7.71(d, J=9 Hz, 1H), 8.11(d, J=8 Hz, 1H)

EXAMPLE 25-2

Synthesis of N-[2-(4-allyl-1-piperazinyl)ethyl]-1-n-propylindazole-3-carboxamide

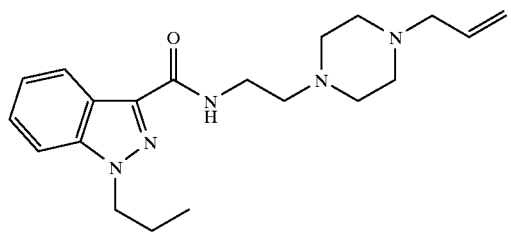

To a solution of N-[2-(4H-1-piperazinyl)ethyl]-1-n-propylindazole-3-carboxamide dihydrochloride (0.39 g) obtained in Example 25-1 in chloroform (5 ml) were successively added at room temperature triethylamine (0.36 g) and allyl bromide (0.14 g) with stirring, and the mixture was stirred at room temperature for 15 hours. The reaction solution was diluted with chloroform (10 ml), and the organic layer was washed with aqueous sodium hydroxide (3 ml). The aqueous layer was extracted with chloroform (10 ml×2), then the combined organic layers were dried over anhydrous sodium sulfate, and concentrated under reduced pressure. The residue (0.28 g) was purified by thin-layer chromatography on silica gel (chloroform:methanol aqueous ammonia=10:1:0.1) to give the title compound (0.17 g) as a colorless oily substance. Yield=48%.

$^1$H NMR(CDCl$_3$) δ 0.96(t, J=7 Hz, 3H), 1.95–2.04(m, 2H), 2.52(bs, 4H), 2.59(bs, 4H), 2.65(t, J=6 Hz, 2H), 3.02(d, J=6 Hz, 2H), 3.59–3.64(m, 2H), 4.36(t, J=7 Hz, 2H), 5.15–5.22(m, 2H), 5.83–5.93(m, 1H), 7.25–7.29(m, 1H), 7.38–7.43(m, 3H), 8.37(d, J=8 Hz,1H)

Then the title compound was converted to the corresponding hydrochloride by a conventional method.

m.p. 190–200° C. (dec.)

$^1$H NMR(D$_2$O) δ 0.88(t, J=8 Hz, 3H), 1.94–2.03(m, 2H), 3.64(t, J=6 Hz, 2H), 3.78(bs, 4H), 3.86(bs, 4H), 3.96–4.00 (m, 2H), 4.48(t, J=7 Hz, 2H), 4.88(d, J=3 Hz, 2H), 5.72–5.76 (m, 2H, 2H), 5.96–6.06(m, 1H, 2H), 7.42(t, J=7 Hz, 1H), 7.58(t, J=7 Hz, 1H), 7.72(d, J=9 Hz, 1H), 8.12(t, J=8 Hz, 1H)

EXAMPLE 26

N-[2-(4-n-Propyl-1-piperazinyl)ethyl]-1-n-propylindazole-3-carboxamide

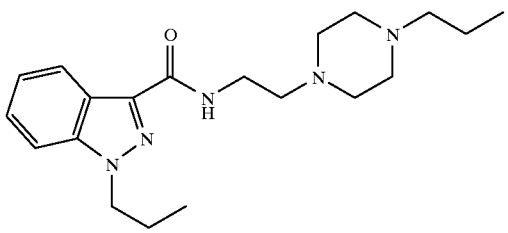

The title compound was synthesized by using N-[2-(4H-1-piperazinyl)ethyl]-1-n-propylindazole-3-carboxamide dihydrochloride obtained in Example 25-1 and 1-bromopropane according to the same process as in Example 25-2.

$^1$H NMR(CDCl$_3$) δ 0.91(t, J=7 Hz, 3H), 0.96(t, J=7 Hz, 3H), 1.48–1.57(m, 2H), 1.94–2.03(m, 2H), 2.32(t, J=8 Hz, 2H), 2.52(bs, 4H), 2.59(bs, 4H), 2.65(t, J=6 Hz, 2H), 3.59–3.64 (m, 2H), 4.36(t,J=7 Hz, 2H), 7.25–7.29(m, 1H), 7.38–7.43(m,3H), 8.37(d, J=8 Hz, 1H)

Then the title compound was converted to the corresponding hydrochloride by a conventional method.

m.p. 185–194° C. (dec.)

$^1$H NMR(D$_2$O) δ 0.88(t, J=8 Hz, 3H), 1.06(t, J=7 Hz, 3H), 1.81–1.91(m, 2H), 1.94–2.03(m, 2H), 3.33(t, J=8 Hz, 2H), 3.65(t, J=6 Hz, 2H), 3.97(m, 2H), 3.60–4.10(br, 8H), 4.48(t, J=7 Hz, 2H), 7.42(t, J=8 Hz, 1H), 7.58(t, J=7 Hz, 1H), 7.72(d, J=9 Hz, 1H), 8.12(d, J=8 Hz, 1H)

EXAMPLE 27

N-[2-(4-n-Pentyl-1-piperazinyl)ethyl]-1-n-propylindazole-3-carboxamide

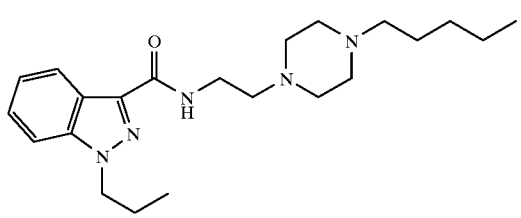

The title compound was synthesized by using N-[2-(4H-1-piperazinyl)ethyl]-1-n-propylindazole-3-carboxamide dihydrochloride obtained in Example 25-1 and n-pentyl bromide according to the same process as in Example 25-2.

$^1$H NMR(CDCl$_3$) δ 0.90(t, J=7 Hz, 3H), 0.95(t, J=7 Hz, 3H), 1.26–1.36(m, 4H), 1.46–1.54(m, 2H), 1.95–2.01(m, 2H), 2.34(t, J=7 Hz, 2H), 2.52(bs, 4H), 2.58(bs, 4H), 2.65(t, J=6 Hz, 2H), 3.59–3.64(m, 2H), 4.35(t, J=7 Hz, 2H), 7.24–7.29(m, 1H), 7.37–7.42(m, 3H), 8.37(d, J=8 Hz, 1H)

Then the title compound was converted to the corresponding hydrochloride by a conventional method.

m.p. 175–183° C. (dec.)

$^1$H NMR(D$_2$O) δ 0.87(t, J=7 Hz, 3H), 0.93(t, J=7 Hz, 3H), 1.40(bs, 4H), 1.81(bs, 2H), 1.93–2.02(m, 2H), 3.33(t, J=8 Hz, 2H), 3.50–3.95(br, 8H), 3.61(t, J=6 Hz, 2H), 3.95(t, J=6 Hz, 2H), 4.49(t, J=7 Hz, 2H), 7.42(t, J=7 Hz, 1H), 7.58(t, J=7 Hz, 1H), 7.74(d, J=9 Hz,1H), 8.13(d, J=8 Hz, 1H)

EXAMPLE 28

N-[2-(4-p-Methoxybenzyl-1-piperazinyl)ethyl]-1-n-propylindazole-3-carboxamide

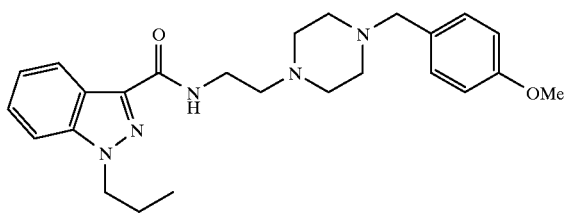

The title compound was synthesized by using N-[2-(4H-1-piperazinyl)ethyl]-1-n-propylindazole-3-carboxamide dihydrochloride obtained in Example 25-1 and p-methoxybenzyl chloride according to the same process as in Example 25-2.

$^1$H NMR(CDCl$_3$) δ 0.96(t, J=7 Hz, 3H), 1.94–2.03(m, 2H), 2.50(bs, 4H), 2.56(bs, 4H), 2.64(t, J=6 Hz, 2H), 3.47(s, 2H), 3.58–3.63(m, 2H), 3.80(s, 3H), 4.36(t, J=7 Hz, 2H), 6.85(d, J=9 Hz, 2H), 7.23(d, J=9 Hz, 2H), 7.25–7.30(m, 1H), 7.38–7.43(m, 3H), 8.37(d,J=8 Hz, 1H)

Then the title compound was converted to the corresponding hydrochloride by a conventional method.

m.p. 177–190° C. (dec.)

$^1$H NMR(D$_2$O) δ 0.88(t, J=7 Hz, 3H), 1.94–2.03(m, 2H), 3.60–3.90(br, 8H), 3.63(t, J=6 Hz, 2H), 3.92(s, 3H), 3.96(t, J=6 Hz, 2H), 4.46–4.50(m, 4H), 7.14(d, J=9 Hz, 2H), 7.42(t, J=8 Hz, 1H), 7.52(d, J=9 Hz, 1H), 7.59(t, J=7 Hz, 1H), 7.73(d, J=9 Hz, 1H), 8.12(d, J=8 Hz, 1H)

EXAMPLE 29

N-[2-(4-n-Butyl-1-piperazinyl)ethyl]-1-ethylindazole-3-carboxamide

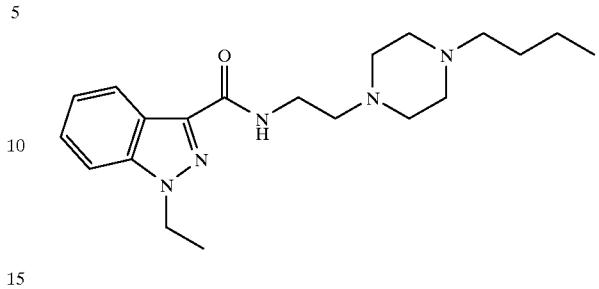

The title compound was synthesized by using N-[2-(4-n-butyl-1-piperazinyl)ethyl]-1H-indazole-3-carboxamide carboxamide obtained in Example 10 and ethyl bromide according to the same process as in Example 12.

$^1$H NMR(CDCl$_3$) δ 0.92(t, J=7 Hz, 3H), 1.28–1.37(m, 2H), 1.45–1.52(m, 2H), 1.56(t, J=7 Hz, 3H), 2.34(t, J=8 Hz, 2H), 2.53(bs, 4H), 2.58(bs, 4H), 2.65(t, J=6 Hz, 2H), 3.59–3.64(m, 2H), 4.45(q,J=7 Hz, 2H), 7.25–7.43(m, 4H), 8.38(d, J=8 Hz, 1H)

Then the title compound was converted to the corresponding hydrochloride by a conventional method.

m.p. 197–206° C. (dec.)

$^1$H NMR(D$_2$O) δ 0.99(t, J=8 Hz, 3H), 1.40–1.50(m, 2H), 1.53(t, J=7 Hz, 3H), 1.76–1.83(m, 2H), 3.35(t, J=8 Hz, 2H), 3.62(t, J=6 Hz, 2H), 3.96(t, J=6 Hz, 2H), 3.60–4.00(br, 8H), 4.55(q, J=7 Hz, 2H), 7.40–7.44(m, 1H), 7.58(t, J=8 Hz, 1H), 7.73(d, J=8 Hz, 1H), 8.12(d, J=8 Hz, 1H)

EXAMPLE 30

N-[2-(4-n-Butyl-1-piperazinyl)ethyl]-1-isopropylindazole-3-carboxamide

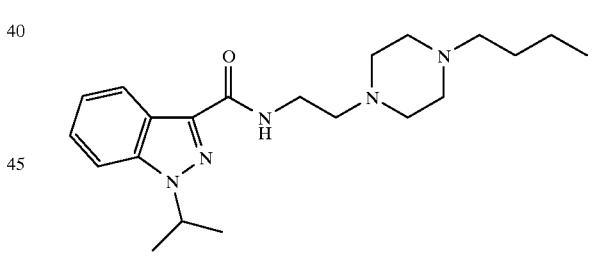

The title compound was synthesized by using N-[2-(4-n-butyl-1-piperazinyl)ethyl]-1H-indazole-3-carboxamide obtained in Example 10 and isopropyl bromide according to the same process as in Example 12.

m.p. 82–84° C.

$^1$H NMR(CDCl$_3$) δ 0.92(t, J=7 Hz, 3H), 1.28–1.38(m, 2H), 1.45–1.53(m, 2H), 1.62(d, J=7 Hz, 6H), 2.35(t, J=8 Hz, 2H), 2.52(bs, 4H), 2.60(bs, 4H), 2.66(t, J=6 Hz, 2H), 3.59–3.64(m, 2H), 4.88(sept, J=7 Hz, 1H), 7.25–7.49(m, 4H), 8.38(d, J=8 Hz, 1H)

Then the title compound was converted to the corresponding hydrochloride by a conventional method.

m.p. 182–194° C. (dec.)

$^1$H NMR(D$_2$O) δ 1.00(t, J=7 Hz, 3H), 1.42–1.51(m, 2H), 1.62(d, J=7 Hz, 6H), 1.77–1.85(m, 2H), 3.36(t, J=8 Hz, 2H), 3.60–4.00(br,8H), 3.65(t, J=6 Hz, 2H), 3.98(t, J=6 Hz, 2H), 5.11(sept, J=7 Hz, 1H), 7.42(t, J=8 Hz, 1H), 7.56–7.60(m, 1H), 7.78(d, J=9 Hz, 1H), 8.14(d, J=8 Hz, 1H)

EXAMPLE 31

N-[2-(4-n-Butyl-1-piperazinyl)ethyl]-1-cyclopentylindazole-3-carboxamide

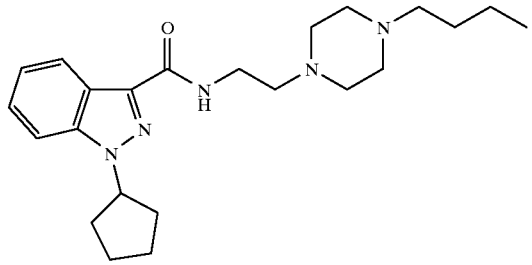

To a solution of N-[2-(4-n-butyl-1-piperazinyl)-ethyl]-1H-indazole-3-carboxamide (0.42 g) obtained in Example 10 in THF (10 ml) were successively added cyclopentanol (0.16 g), triphenylphosphine (0.41 g) and diethyl azodicarboxylate (0.36 g) under ice-cooling, and then the mixture was stirred at room temperature for 22 hours. The residue obtained by concentration of the reaction solution was purified by silica gel column chromatography (methylene chloride:ethyl acetate=1:1-chloroform:methanol:aqueous ammonia=10:1:0.05) to give a fraction (0.47 g) containing the title compound. This fraction was separated by thin-layer chromatography on silica gel (chloroform:methanol:aqueous ammonia=10:1:0.1) to give the title compound (0.36 g) as a pale yellow oily substance. Yield=71%.

$^1$H NMR(CDCl$_3$) δ 0.93(t, J=7 Hz, 3H), 1.29–1.38(m, 2H), 1.44–1.51(m, 2H ), 1.53–2.26(m, 8H), 2.34(t, J=8 Hz, 2H), 2.58(bs, 8H), 2.65(t, J=6 Hz, 2H), 3.57–3.64(m, 2H), 5.00–5.07(m, 1H), 7.24–7.28(m, 1H), 7.37–7.48(m, 3H), 8.37(d, J=8 Hz, 1H)

Then the title compound was converted to the corresponding hydrochloride by a conventional method.

m.p. 157–174° C. (dec.)

$^1$H NMR(D$_2$O) δ 1.00(t, J=7 Hz, 3H), 1.41–1.51(m, 2H), 1.53–2.29(m, 10H), 3.36(t, J=8 Hz, 2H), 3.63(bs, 2H), 3.79(bs, 8H), 3.94–4.00(m, 2H), 5.16–5.21(m, 1H), 7.39(t, J=7 Hz, 1H), 7.54(t,J=8 Hz, 1H), 7.73(d, J=8 Hz, 1H), 8.09(d, J=7 Hz, 1H)

EXAMPLE 32

N-[2-(4-n-Butyl-1-piperazinyl)ethyl]-1-n-propylindazole-3-thiocarboxamide

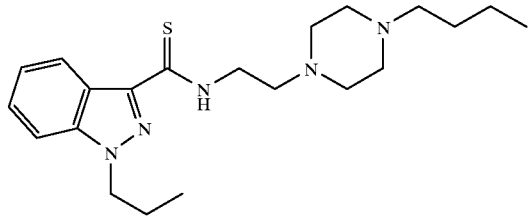

To a solution of N-[2-(4-n-butyl-1-piperazinyl)-ethyl]-1-n-propylindazole-3-carboxamide (0.39 g) obtained in Example 3 in toluene (10 ml) was added Lawesson reagent (0.64 g) at room temperature, and the mixture was heated under reflux for one hour. The reaction solution was cooled to room temperature, diluted with chloroform (50 ml), and then washed with saturated aqueous sodium hydrogencarbonate (50 ml). The organic layer was dried over anhydrous sodium sulfate, and concentrated under reduced pressure. The residue was purified by thin-layer chromatography on silica gel (chloroform:methanol:aqueous ammonia=8:2:0.2) to give the title compound (0.36 g) as a pale yello; oily substance. Yield=88%.

$^1$H NMR(CDCl$_3$) δ 0.91(t, J=7 Hz, 3H), 0.96(t, J=7 Hz, 3H), 1.28–1.37(m, 2H), 1.63(bs, 2H), 1.95–2.04(m, 2H), 2.83(bs, 4H), 2.60–3.10(br, 8H; piperazine-H), 3.96(bs, 2H), 4.36(t, J=7 Hz, 2H), 7.28–7.32(m, 1H), 7.41–7.42(m, 3H), 8.87(d, J=8 Hz, 1H)

Then the title compound was converted to the corresponding hydrochloride by a conventional method.

m.p. 178–186° C. (dec.)

$^1$H NMR(D$_2$O) δ 0.88(t, J=7 Hz, 3H), 1.00(t, J=7 Hz, 3H), 1.45–1.47(m, 2H), 1.80(bs, 2H), 1.98–2.00(m, 2H), 3.35(bs, 2H), 3.77(bs, 2H), 3.45–4.10(br, 8H), 4.41(bs, 2H), 4.49(bs, 2H), 7.43(t,J=7 Hz, 1H), 7.58(t, J=7 Hz, 1H), 7.72(d, J=8 Hz, 1H), 8.56(d, J=8 Hz, 1H)

EXAMPLE 33

3-{N-[ 2-(4-n-Butyl-1-piperazinyl)ethyl]aminomethyl}-1-n-propylindazole

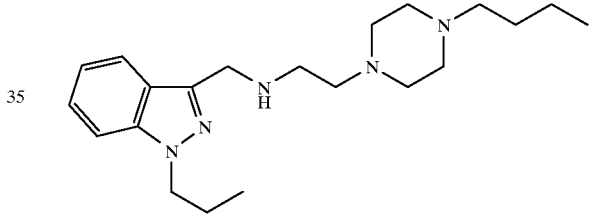

To a solution of N-[2-(4-n-butyl-1-piperazinyl)-ethyl]-1-n-propylindazole-3-carboxamide (0.36 g) obtained in Example 3 in THF (5 ml) was added lithium aluminum hydride (0.11 g) at room temperature, and the mixture was heated under reflux for 3 hours. The reaction solution was ice-cooled, and were successively added water (0.1 ml), a 15% aqueous sodium hydroxide (0.1 ml), water (0.3 ml) and THF (10 ml). After the reaction solution was stirred at room temperature for 30 minutes, the insolubles were filtered off with Celite. The filtrate was distilled off under reduced pressure, and the residue was purified by thin-layer chromatography on silica gel (chloroform:methanol:aqueous ammonia=8:2:0.2) to give the title compound (0.14 g) as a pale yellow oily substance. Yield=40%.

$^1$H NMR(CDCl$_3$) δ 0.89–0.94(m, 6H), 1.24–1.35(m, 2H), 1.41–1.49(m, 2H), 1.81(bs, 1H), 1.87–1.98(m, 2H), 2.29(t, J=8 Hz, 2H), 2.41(bs, 8H), 2.50(t, J=6 Hz, 2H), 2.77(t, J=6 Hz, 2H), 4.17(s, 2H), 4.30(t, J=7 Hz, 2H), 7.10–7.14(m, 1H), 7.35–7.36(m, 2H), 7.78(d, J=8.3 Hz, 1H)

Then the title compound was converted to the corresponding hydrochloride by a conventional method.

m.p. 104–119° C. (dec.)

$^1$H NMR(D$_2$O) δ 0.84(t, J=7 Hz, 3H), 0.95(t, J=7 Hz, 3H), 1.34–1.44(m, 2H), 1.63–1.71(m, 2H), 1.88–1.97(m, 2H), 2.60–3.60(br,8H), 2.96(t, J=6 Hz, 2H), 3.11(t, J=8 Hz, 2H), 3.37(t, J=6 Hz, 2H), 4.46(t, J=7 Hz, 2H), 4.72(s, 2H), 7.38(t, J=8 Hz, 1H), 7.60(t, J=8 Hz, 1H), 7.73(d, J=9 Hz, 1H), 7.93(d, J=8 Hz, 1H)

EXAMPLE 34

The agonist activities of the indazole derivatives of the present invention and Mosapride were determined by the following method, that is, the method determining 5-$HT_4$ agonist activity by using rat oesophageal tunica muscularis mucosae (Naunyn-Schmiedeberg's Arch. Pharmacol., Vol. 343, 439–446, 1991).

According to the method of the literature, the oesophageal tunica muscularis mucosae excised from rats were suspended in an organ bath containing Krebs-Henseleit solution aerated with a mixed gas (95% $O_2$, 5% $CO_2$) and contracted with carbachol ($1 \times 10^{-6}$M). After the contraction was stabilized, the cumulative administration of the compounds was performed to determine the relaxation of the rat oesophagus pre-contracted with carbachol. The concentration ($ED_{50}$) to cause 50% relaxation of the carbachol-induced contraction was measured. The result is expressed in terms of -log $ED_{50}$ and shown in the following table in which higher numerical value indicates higher activity.

TABLE 1

| Compound of Example No. | $R_1$ | Q | $R_2$ | m, n, o | $R_3$ | Activity (-log $ED_{50}$) |
|---|---|---|---|---|---|---|
| Compound 1 | n-Pr | C = O | III | n:3 | n-Bu | 4.98 |
| Compound 2 | n-Pr | C = O | III | n:2 | Me | 4.69 |
| Compound 3 | n-Pr | C = O | III | n:2 | n-Bu | 5.62 |
| Compound 4 | n-Pr | C = O | IV | o:1 | Me | 5.01 |
| Compound 5 | n-Pr | C = O | IV | o:1 | n-Bu | 6.36 |
| Compound 6 | n-Pr | C = O | V | m:0 | n-Bu | 5.19 |
| Compound 7 | n-Pr | C = O | II | m:1 | Me | 5.30 |
| Compound 8 | n-Pr | C = O | II | m:2 | Me | 4.97 |
| Compound 9 | H | C = O | IV | o:1 | p-FBn | 5.13 |
| Compound 11 | H | C = O | III | n:2 | p-FBn | 4.90 |
| Compound 12 | n-Pr | C = O | IV | o:1 | p-FBn | 5.47 |
| Compound 13 | sec-Bu | C = O | III | n:2 | n-Bu | 5.26 |
| Compound 14 | 3-Pentyl | C = O | III | n:2 | n-Bu | 5.22 |
| Compound 15 | n-Pr | C = O | III | n:2 | p-FBn | 5.17 |
| Compound 16 | allyl | C = O | III | n:2 | p-FBn | 5.13 |
| Compound 17 | n-Pr | C = O | II | m:0 | Bn | 5.47 |
| Compound 18 | n-Pr | C = O | II | m:1 | n-Bu | 5.10 |
| Compound 19 | n-Pr | C = O | II | m:2 | n-Bu | 5.89 |
| Compound 20 | n-Pr | C = O | II | m:0 | H | 3.95 |
| Compound 21 | n-Pr | C = O | II | m:1 | H | 4.32 |
| Compound 22 | n-Pr | C = O | II | m:0 | Me | 5.16 |
| Compound 23 | n-Pr | C = O | II | m:0 | n-Bu | 5.55 |
| Compound 25 | n-Pr | C = O | III | n:2 | allyl | 5.22 |
| Compound 26 | n-Pr | C = O | III | n:2 | n-Pr | 5.05 |
| Compound 27 | n-Pr | C = O | III | n:2 | n-Pentyl | 5.57 |
| Compound 28 | n-Pr | C = O | III | n:2 | p-MeOBn | 5.80 |
| Compound 29 | Et | C = O | III | n:2 | n-Bu | 4.99 |
| Compound 30 | i-Pr | C = O | III | n:2 | n-Bu | 5.53 |
| Compound 31 | cyc-Pentyl | C = O | III | n:2 | n-Bu | 5.30 |
| Compound 32 | n-Pr | C = S | III | n:2 | n-Bu | 4.98 |
| Compound 33 | n-Pr | $CH_2$ | III | n:2 | n-Bu | 4.53 |
| Mosapride | | | | | | 4.46 | note) Bn: benzyl
p-FBn: p-fluorobenzyl
p-MeOBn: p-methoxybenzyl

Finally, examples of pharmaceutical preparations comprising as an active ingredient the present compounds (all the hydrochlorides) are given below.

Pharmaceutical Preparation 1

| Tablets (one tablet) | |
|---|---|
| Compound of Example 3 | 10 mg |
| Lactose | 64 mg |
| Crystalline cellulose | 15 mg |
| Corn starch | 7 mg |
| Hydroxypropylcellulose | 3 mg |
| Magnesium stearate | 1 mg |

All components were uniformly mixed to form powders for direct compression. The powders were formed in a rotary tableting machine to tablets each having 6 mm in diameter and 100 mg in weight.

Pharmaceutical Preparation 2

| Sugar-coated tablets (one tablet) | | |
|---|---|---|
| A: | Compound of Example 3 | 10 mg |
| | Lactose | 64 mg |
| | Crystalline cellulose | 15 mg |
| | Corn starch | 7 mg |
| | Hydroxypropylcellulose | 3 mg |
| | Magnesium stearate | 1 mg |
| B: | Saccharose | 92 mg |
| | Gum arabic | 3.2 mg |
| | Gelatin | 0.7 mg |
| | Calcium carbonate | 20 mg |

All components of the above group A were uniformly mixed to form powders for direct compression. The powders were formed in a rotary tableting machine to tablets each having 6 mm in diameter and 100 mg in weight. The tablets were coated with the components of the above group B according to a conventional method to prepare the sugar-coated tablets.

Pharmaceutical Preparation 3

| Hard capsules (per capsule) | |
|---|---|
| Compound of Example 3 | 10 mg |
| Lactose | 64 mg |
| Crystalline cellulose | 15 mg |
| Corn starch | 7 mg |
| Hydroxypropylcellulose | 3 mg |
| Magnesium stearate | 1 mg |

All components were uniformly mixed, pressed and pulverized to prepare granules. The granules were filled in a capsule to prepare a hard capsule.

Pharmaceutical Preparation 4

| Granules (per divided packet) | | |
|---|---|---|
| A: | Compound of Example 3 | 10 mg |
| | Lactose | 90 mg |
| | Crystalline cellulose | 50 mg |
| | Corn starch | 50 mg |
| B: | Hydroxypropylcellulose | 10 mg |
| | Ethanol | 9 mg |

After all components of the above group A were uniformly mixed, a solution of the above group B was added.

The mixture was kneaded and granulated by an extrusion granulation method. The granules were then dried in a drier at 50° C. The dried granules were screened to granule sizes of 297 μm–1460 μm to give a granule formulation containing 200 mg net weight per divided packet.

Pharmaceutical Preparation 5

|  Syrups  |  |
| --- | --- |
| Compound of Example 3 | 1.000 g |
| Refined sugar | 30.000 g |
| D-sorbitol, 70 w/v % | 25.000 g |
| Ethyl paraoxybenzoate | 0.030 g |
| Propyl paraoxybenzoate | 0.015 g |
| Flavor | 0.200 g |
| Glycerin | 0.150 g |
| 96% Ethanol | 0.500 g |
| Distilled water | q.s. to make up a total amount 100 ml |

The active ingredient, refined sugar, D-sorbitol, ethyl paraoxybenzoate and propyl paraoxybenzoate were dissolved in 60 g of wiarm water. After cooling, glycerol and a solution of flavor in ethanol were added. Then distilled water was added to the mixture to make up a total amount of 100 ml.

Pharmaceutical Preparation 6

| Injections |  |
| --- | --- |
| Compound of Example 3 | 1 mg |
| Sodium chloride | 10 mg |
| Distilled water | q.s. to make up a total amount 1.0 ml |

The active ingredient and sodium chloride were dissolved in distilled water to make up a total amount of 1.0 ml.

Pharmaceutical Preparation 7

| Suppositories (per piece) |  |
| --- | --- |
| Compound of Example 3 | 2 g |
| Polyethylene glycol 4000 | 20 g |
| Glycerol | 78 g |

The active ingredient was dissolved in gylcerol. To the solution was added polyethylene glycol 4000 and the mixture was warmed to be a solution. The solution was poured into a suppository mold and solidified by cooling to prepare suppositories weighing 1.5 g per piece.

Industrial Applicability

The indazole derivatives (I) having a monocyclic amine or pharmaceutically acceptable salts thereof provided by the present invention have a 5-HT$_4$ receptor agonistic activity and are useful for the treatment of digestive tract disorders derived from chronic gastritis, diabetes mellitus, gastrectomy, peptic ulcer and scleroderma, and digestive tract diseases including reflux esophagitis, irritable bowel syndrome and spurious ileus.

We claim:
1. An indazole compound of the formula (I):

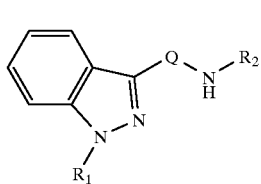

(I)

wherein
R$_1$ is hydrogen, C$_1$–C$_6$ alkyl, C$_3$–C$_6$ alkenyl or C$_3$–C$_6$ cycloalkyl;
Q is carbonyl, thiocarbonyl or methylene; and
R$_2$ is a group of the formula (II) or (IV):

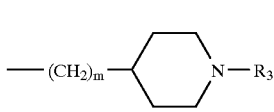

(II)

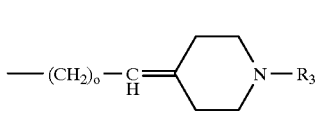

(IV)

wherein R$_3$ is C$_1$–C$_6$ alkyl, C$_3$–C$_6$ alkenyl or benzyl, of which a phenyl ring thereof is optionally mono- or di- substituted by the same or different halogen or methoxy; m is 0 to 2; and o is 1 or 2; or a pharmaceutically acceptable salt thereof.

2. The compound of claim 1, where R$_1$ is C$_1$–C$_6$ alkyl, Q is carbonyl, and R$_2$ is a group of the formula (II):

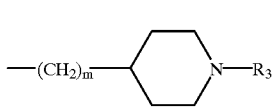

(II)

wherein R$_3$ is C$_1$–C$_6$ alkyl or benzyl, of which a phenyl ring thereof is optionally mono- or di- substituted by the same or different halogen atom, and m is 0 to 2, or a pharmaceutically acceptable salt thereof.

3. The compound of claim 1, where R$_1$ is hydrogen, C$_1$–C$_6$ alkyl or C$_3$–C$_6$ alkenyl; Q is carbonyl, and R$_2$ is a group of the formula (IV):

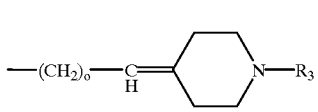

(IV)

wherein R$_3$ is C$_1$–C$_6$ alkyl or benzyl, of which a phenyl ring thereof is optionally mono- or di- substituted by the same or different halogen atom, and o is 0 or 2, or a pharmaceutically acceptable salt thereof.

4. The compound of claim 1, which is N-(1-n-butyl-4-piperdyl)-1-n-propylindazole-3-carboxamide, N-[2-(1-n-butyl-4-piperidyl)ethyl]-1-n-propylindazole-3-carboxamide, or N-[2-(1-n-butyl-4-piperidylidene)ethyl]-1-n-propylindazole-3-carbxamide, or a pharmaceutically acceptable salt thereof.

5. The compound of claim 4, which is N-(1-n-butyl-4-piperidvl)-1-n-propylindazole-3-carboxamide.

6. The compound of claim 4, which is N-[2-(1-n-butyl-4-piperidyl)ethyl]-1-n-propylindazole-3-carboxamide.

7. The compound of claim 4, which is N-[2-(1-n-butyl-4-piperidylidene)ethyl]-1-n-propylindazole-3-carboxamide.

8. A pharmaceutical composition, which comprises as an active ingredient one or more compounds of claim 1, or a pharmaceutically acceptable salt or salts thereof, in admixture with a pharmaceutically acceptable additive.

9. A 5-$HT_4$ receptor agonist, which comprises as an active ingredient one or more compounds of claim 1, or a pharmaceutically acceptable salt or salts thereof, in admixture with a pharmaceutically acceptable additive.

10. A method of treating digestive tract disorders, which comprises administering to a patient in need thereof one or more compounds of claim 1, or a pharmaceutically acceptable salt or salts thereof.

11. The method of claim 10, which promotes gastrointestinal motility.

* * * * *

UNITED STATES PATENT AND TRADEMARK OFFICE
CERTIFICATE OF CORRECTION

PATENT NO. : 5,945,434
DATED : AUGUST 31, 1999
INVENTOR(S) : MASASHI SUZUKI ET AL

It is certified that error appears in the above-identified patent and that said Letters Patent is hereby corrected as shown below:

Column 66, line 63, "piperdyl" should be - -piperidyl- -.

Signed and Sealed this

Twenty-third Day of May, 2000

Attest:

Q. TODD DICKINSON

*Attesting Officer*          *Director of Patents and Trademarks*